United States Patent [19]
Cercek et al.

[11] Patent Number: 5,516,643
[45] Date of Patent: May 14, 1996

[54] IMMUNOCHEMICAL ASSAYS FOR CANCER-ASSOCIATED SCM-RECOGNITION FACTOR

[76] Inventors: Boris Cercek; Lea Cercek, both of 4318 Camphor Ave., Yorba Linda, Calif. 92686

[21] Appl. No.: 161,176

[22] Filed: Dec. 3, 1993

Related U.S. Application Data

[63] Continuation of Ser. No. 927,534, Aug. 10, 1992, abandoned, which is a continuation-in-part of Ser. No. 539,686, Jun. 18, 1990, Pat. No. 5,270,171, which is a continuation-in-part of Ser. No. 167,007, Mar. 11, 1988, abandoned, which is a continuation-in-part of Ser. No. 22,759, Mar. 6, 1987, abandoned.

[51] Int. Cl.$^6$ .................. G01N 33/53; G01N 33/574
[52] U.S. Cl. .................. 435/7.23; 435/7.1; 435/7.21; 435/7.92; 435/240.26; 436/63; 436/64; 436/518; 530/387.7; 530/387.9; 530/388.8; 530/388.85
[58] Field of Search .................. 530/326, 7.1, 7.2, 530/7.21, 7.23, 7.5, 7.92, 7.93, 7.94, 7.95, 240.26, 960, 387.1, 387.7, 387.9, 388.25, 388.1, 388.2, 388.24, 388.26; 436/501, 518, 524, 63, 64; 435/7.23

[56] References Cited

U.S. PATENT DOCUMENTS

| | | | |
|---|---|---|---|
| 4,444,744 | 9/1982 | Goldenberg | 424/1.1 |
| 4,645,738 | 9/1983 | Knowles et al. | 435/7.9 |

FOREIGN PATENT DOCUMENTS

| | | |
|---|---|---|
| WO8707382 | 12/1987 | WIPO . |
| WO8806595 | 9/1988 | WIPO . |
| WO8908662 | 9/1989 | WIPO . |
| WO9004785 | 5/1990 | WIPO . |
| WO8908118 | 9/1992 | WIPO . |

OTHER PUBLICATIONS

Dengler et al (Jul. 1992) Biol. Chem. Hoppe-Seyler. 373: 581–588.
L. Cercek et al., "Biophysical Differentiation Between Lymphocytes from Healthy Donors, Patients with Malignant Diseases and Other Disorders," *Brit. J. Cancer* 29:345–352 (1974).
L. Cercek & B. Cercek, "Application of the Phenomenon of Changes in the Structuredness of Cytoplasmic Matrix (SCM) in the Diagnosis of Malignant Disorders: a Review," *Europ. J. Cancer* 13:903–915 (1977).
L. Cercek & B. Cercek, "Changes in SCM-Responses of Lymphocytes in Mice After Implantation with Ehrlich Ascites Cells," *Europ. J. Cancer* 17:167–171 (1981).
L. Cercek & B. Cercek, "Changes in the SCM Response Ratio ($RR_{SCM}$) After Surgical Removal of Malignant Tissue," *Brit. J. Cancer* 31:250–251 (1975).
L. Cercek & B. Cercek, "Apparent Tumor Specificity with the SCM Test," *Brit. J. Cancer* 31:252–253 (1975).
S. Chaitchik et al., "Tumor Specificity of the SCM Test for Cancer Diagnosis," *Eur. J. Cancer Clin. Oncol.* 21:1165–1170 (1985).
H. Orjasaeter et al., "Response of T–Lymphocytes to Phytohaemagglutinin (PHA) and to Cancer–Tissue–Associated Antigens, Measured by the Intracellular Fluorescence Polarization Technique (SCM Test)," *Br. J. Cancer* 40:628–633 (1979).
L. Cercek & B. Cercek, "Effects of Ascorbate Ions on Intracellular Fluorescein Emission Polarization Spectra in Cancer and Normal Proliferating Cells," *Cancer Detection and Prevention* 10:1–20 (1987).
K. Suzuki & Y. Sasaki, "Studies on Encephalitogenic Fragments of Myelin Protein. IV. Synthesis of Glycine Analogs of Tryptophan–Containing Fragment," *Chem. Pharm. Bull.* 22:2181–2187 (1974).
A. A. Gershkovich et al., "A Study of the Properties of Synthetic Analogs of the Tryptophan–Containing Fragment 113–121 of the Basic Protein of Myelin," *Khim. Prirod. Soedinen.* 4:557–565 (1979) (translated from Russian).
C. M. Deber & M. E. M. Young, "Association of Carbon–13 Enriched Human Encephalitogenic Nonapeptide with a Membrane Surface," *J. Biol. Chem.* 254:6341–6345 (1979).
C. Blake & B. J. Gould, "Use of Enzymes in Immunoassay Techniques: A Review," *Analyst* 109:533–547 (1984).
M. Oellerich, "Enzyme–Immunoassay: A Review," *J. Clin. Chem. Clin. Biochem.* 22:895–904 (1984).
J. L. Marx, "How Cancer Cells Spread in the Body," *Science* 244:147–148 (1989).
B. W. Hancock & R. C. Rees, "Interleukin–2 and Cancer Therapy," *Cancer Cells* 2:29–32 (1990).
J. G. Kaplan & C. Bona, "Proteases as Mitogens: The Effect of Trypsin and Pronase on Mouse and Human Lymphocytes," *Exp. Cell Res.* 88:388–394 (1974).

(List continued on next page.)

*Primary Examiner*—Toni R. Scheiner
*Attorney, Agent, or Firm*—Merhant, Gould, Smith, Edell, Welter & Schmidt

[57] ABSTRACT

Disclosed are antibodies to peptides active in the structuredness of the cytoplasmic matrix test (SCM-factor peptides) and to fragments of the peptides by immunization of antibody-producing animals with the peptides or fragments. Both polyclonal and monoclonal antibodies can be prepared. Particularly useful are antibodies specifically binding the peptides M-I-P-P-E-V-K-F-N-K-P-F-V-F-L-M-I-D-Q-N-T-K-V-P-L-F-M-G-K (SEQ ID NO: 2) and F-L-M-I-D-Q-N-T-K (SEQ ID NO: 3). The antibodies can be labeled and are suitable for performing immunoassays to detect the presence of SCM cancer-recognition factors in cell cultures or body fluids. One particularly useful immunoassay can distinguish SCM factor from partially homologous peptide sequences, and comprises: (a) incubating a first aliquot of the sample with a first antibody specific for the cancer-recognition factor to bind the first antibody to the cancer-recognition factor in the first aliquot; (b) reacting a second aliquot of the sample with a second antibody specific for the amino-terminal portion of the partially homologous peptide sequence to bind the second antibody to the partially homologous peptide sequence in the second aliquot; and (c) comparing the quantity of the first antibody bound to the first aliquot with the quantity of the second antibody bound to the second aliquot to detect the cancer recognition factor.

67 Claims, 4 Drawing Sheets

OTHER PUBLICATIONS

Y. Shai et al., "Antisense Peptide Recognition of Sense Peptides: Sequence Simplification and Evaluation of Forces Underlying the Interaction," *Biochemistry* 28:8804–8811 (1989).

G. Fassina et al., "Recognition Properties of Antisense Peptides to $Arg^8$–Vasopressin/Bovine Neurophysin II. Biosynthetic Precursor Sequences," *Biochemistry* 28:8811–8818 (1989).

M. R. Potter & M. Moore, "Natural Cytotoxic Reactivity of Human Lymphocyte Subpopulations," *Immunology* 37:187–194 (1979).

J. L. Marx, "What T Cells See and How They See It." *Science* 242:863–865 (1988).

W. Becker, "Determination of Antisera Titres Using the Single Radial Immunodiffusion Method," *Immunochemistry* 6:539–546 (1969).

R. W. Carrell et al., "Structure and Variation of Human $\alpha_1$–Antitrypsin," *Nature* 298:329–334 (1982).

M. Fagerhol & D. W. Cox, "The Pi Polymorphism; Genetic, Biochemical, and Clinical Aspects of Human $\alpha_1$–Antitrypsin," in *Advances in Human Genetics* (H. Harris and K. Hirschhorn, eds., Plenum Press, New York, 1981), vol. 11, pp. 1–62.

W. Troll, M. S. Meyn & T. G. Rossman, "Mechanisms of Protease Action in Carcinogenesis," in *Carcinogenesis—A Comprehensive Survey, vol. II; Mechanisms of Tumor Promotion and Cocarcinogenesis* (T. J. Slaga et al., eds., Raven Press, New York, 1978), pp. 301–312.

T. G. Rossman & W. Troll, "Protease Inhibitors in Carcinogenesis: Possible Sites of Action," in *Carcinogenesis, vol. V: Modifiers of Chemical Carcinogenesis* (T. J. Slaga, ed., Raven Press, New York, 1980), pp. 127–148.

G. J. Cianciolo, "Anti–Inflammatory Effects of Neoplasia," in *Inflammation: Basic Principles and Clinical Correlates* (J. I. Gallin et al., eds., Raven Press, New York, 1988), ch. 48, pp. 861–874.

E. Reich, "Tumor–Associated Fibrinolysis," *Fed. Proc.* 32:2174–2175 (1973).

H. B. Bosmann, "Release of Specific Protease During Mitotic Cycle of L5178Y Murine Leukaemic Cells by Sublethal Autolysis," *Nature* 249:144–145 (1974).

D. Moscatelli & D. B. Rifkin, "Membrane and Matrix Localization of Proteinase: A Common Theme in Tumor Cell Invasion and Angiogenesis," *Biochim. Biophys. Acta* 948:67–85 (1988).

B. Hagmar et al.,"Why Do Tumors Metastasize? An Overview of Current Research," *Tumor Biol.* 5:141–149 (1984).

C. A. McWherter et al., "Novel Inhibitors of Human Leukocyte Elastase and Cathepsin G. Sequence Variants of Squash Seed Protease Inhibitor with Altered Protease Selectivity," *Biochemistry* 28:5708–5714 (1989).

D. C. Linch et al., "Signal Transduction in Human T Lymphocytes," *Immunol. Rev.* 95:137–159 (1987).

G. L. Nicolson, "Cancer Metastasis: Tumor Cell and Host Organ Properties Important in Metastasis to Specific Secondary Sites," *Biochim. Biophys. Acta* 948:175–224 (1988).

M. S. Bernatowicz & G. R. Matsueda, "Preparation of Peptide–Protein Immunogens Using N–Succinimidyl Bromoacetate as a Heterobifunctionl Crosslinking Reagent," *Anal. Biochem.* 155:95–102 (1986).

E. Harlow & D. Lane, "Antibodies: A Laboratory Manual" (Cold Spring Harbor Laboratory, Cold Springs Harbor, New York, 1988), ch. 5, pp. 53–137.

J. W. Goding, "Monoclonal Antibodies: Principles and Practice" (Academic Press, London, 2d ed., 1986), pp. 59–93.

P. Tijssen, "Practice and Theory of Enzyme Immunoassays" (Elsevier, Amsterdam, 1985), pp. 297–314.

C. Wittekind et al., "Localization of CEA, HCG, Lysozyme, Alpha–1–Antitrypsin, and Alpha–1–Antichymotryupsin in Gastric Cancer and Prognosis," *Virchows Arch. A* 409:715–724 (1986).

H. Kataoka et al., "Neutral Proteinase and Inhibitors Secreted by Human Rectal Adenocarcinoma Cell Line (RCM–1)," *Invasion Metastasis* 9:149–166 (1989).

H. Kataoka et al., "New Human Colorectal Carcinoma Cell Lines That Secrete Proteinase Inhibitors in Vitro," *Virchows Archiv B* 57:157–165 (1989).

R. G. Crystal, "$\alpha 1$–Antitrypsin Deficiency, Emphysema, and Liver Disease," *J. Clin. Invest.* 85:1343–1352 (1990).

R. W. Carrell et al., "The Molecular Pathology of the Serpins," *Mol. Biol. Med.* 6:35–42 (1989).

G. L. Long et al., "Complete Sequence of the cDNA for Human $\alpha_1$–Antitrypsin and the Gene for the S Variant," *Biochemistry* 23:4828–4837 (1984).

C. Longstaff & P. J. Gaffney, "Serpin–Serine Protease Binding Kinetics: $\alpha_2$–Antiplasmin as a Model Inhibitor," *Biochemistry* 30:979–986 (1991).

A. E. Mast et al., "Analysis of the Plasma Elimination Kinetics and Conformational Stabilities of Native, Proteinase–Complexed, and Reactive Site Cleaved Serpins: Comparison of $\alpha_1$–Proteinase Inhibitor, $\alpha_1$–Antichymotrypsin, Antithrombin III, $\alpha_2$–Antiplasmin, Angiotensinogen, and Ovalbumin," *Biochemistry* 30: 1723–1730 (1981).

D. H. Perlmutter et al., "Endocytosis and Degradation of $\alpha_1$–Antitrypsin–Protease Complexes is Mediated by the Serpin–Enzyme Complex (SEC) Receptor," *J. Biol. Chem.* 265:1613–1616 (1990).

I. Wilson et al., "The Structure of an Antigenic Determinant," *Cell* 37:767–778 (1984).

M. Bodanszky, "Peptide Chemistry: A Practical Textbook" (Springer–Verlag, Berlin, 1988) ch. 10, pp. 147–168.

T. E. Creighton, "Proteins: Structures and Molecular Properties" (W. H. Freeman, New York, 1984), pp. 110–112.

Kohler et al. (1975) *Nature* 256: 495–497.

FIG. IA
SCM FACTOR ATTACHMENT TO A SOLID PHASE
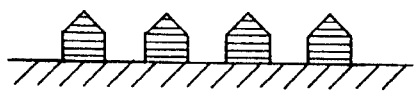
FIG. IB
INCUBATION WITH RABBIT ANTI SCM-FACTOR ANTIBODIES
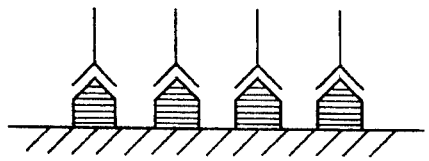
FIG. IC
INCUBATION WITH GOAT ANTI-RABBIT-IgG (ANTIBODY WITH ALP-ENZYME)
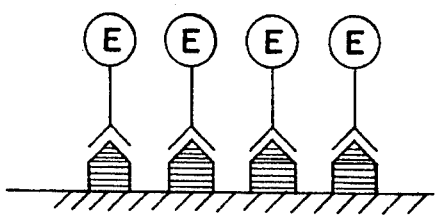
FIG. ID
ADDITION OF P-NITROPHENYLPHOSPHATE (PNP) SUBSTRATE
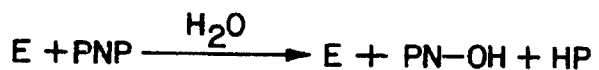
FIG. IE
MEASUREMENTS OF OPTICAL DENSITY (O.D.) AT 405 NM (PN-OH)

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:1:

| Met | Ile | Pro | Pro | Glu | Val | Lys | Phe | Asn | Lys | Pro | Phe | Val | Phe | Leu | Met |
|---|---|---|---|---|---|---|---|---|---|---|---|---|---|---|---|
| 1 | | | | 5 | | | | | 10 | | | | | 15 | |

Ile Asp Gln Asn Thr Lys Val Pro Leu Phe Met Gly Lys Cys
                     20                  25                      30

( 2 ) INFORMATION FOR SEQ ID NO:2:

( i ) SEQUENCE CHARACTERISTICS:
            ( A ) LENGTH: 29 amino acids
            ( B ) TYPE: amino acid
            ( D ) TOPOLOGY: linear ( i i ) MOLECULE TYPE: peptide ( i i i ) HYPOTHETICAL: NO ( v i ) ORIGINAL SOURCE:
            ( A ) ORGANISM: Homo sapiens ( x i ) SEQUENCE DESCRIPTION: SEQ ID NO:2:

Met Ile Pro Pro Glu Val Lys Phe Asn Lys Pro Phe Val Phe Leu Met
    1               5                   10                      15

Ile Asp Gln Asn Thr Lys Val Pro Leu Phe Met Gly Lys
                     20                  25

( 2 ) INFORMATION FOR SEQ ID NO:3:

( i ) SEQUENCE CHARACTERISTICS:
            ( A ) LENGTH: 9 amino acids
            ( B ) TYPE: amino acid
            ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
            ( A ) ORGANISM: Homo sapiens ( x i ) SEQUENCE DESCRIPTION: SEQ ID NO:3:

Phe Leu Met Ile Asp Gln Asn Thr Lys
    1               5

( 2 ) INFORMATION FOR SEQ ID NO:4:

( i ) SEQUENCE CHARACTERISTICS:
            ( A ) LENGTH: 21 amino acids
            ( B ) TYPE: amino acid
            ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
            ( A ) ORGANISM: Homo sapiens ( x i ) SEQUENCE DESCRIPTION: SEQ ID NO:4:

Met Ile Pro Pro Glu Val Lys Phe Asn Lys Pro Phe Val Phe Leu Met
    1               5                   10                      15

Asp Gln Asn Thr Lys
                     20

( 2 ) INFORMATION FOR SEQ ID NO:5:

( i ) SEQUENCE CHARACTERISTICS:
            ( A ) LENGTH: 22 amino acids
            ( B ) TYPE: amino acid (D) TOPOLOGY: linear (ii) MOLECULE TYPE: peptide (iii) HYPOTHETICAL: NO (v) FRAGMENT TYPE: C-terminal (vi) ORIGINAL SOURCE:
    (A) ORGANISM: Homo sapiens (xi) SEQUENCE DESCRIPTION: SEQ ID NO:5:

```
Phe Asn Lys Pro Phe Val Phe Leu Met Ile Asp Gln Asn Thr Lys Val
1               5                   10                  15
Pro Leu Phe Met Gly Lys
            20
```

(2) INFORMATION FOR SEQ ID NO:6:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (iii) HYPOTHETICAL: NO (v) FRAGMENT TYPE: internal (vi) ORIGINAL SOURCE:
    (A) ORGANISM: Homo sapiens (xi) SEQUENCE DESCRIPTION: SEQ ID NO:6:

```
Phe Asn Lys Pro Phe Val Phe Leu Met Ile Asp Gln Asn Thr Lys
1               5                   10                  15
```

(2) INFORMATION FOR SEQ ID NO:7:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (iii) HYPOTHETICAL: NO (v) FRAGMENT TYPE: N-terminal (vi) ORIGINAL SOURCE:
    (A) ORGANISM: Homo sapiens (xi) SEQUENCE DESCRIPTION: SEQ ID NO:7:

```
Met Ile Pro Pro Glu Val Lys Phe Asn Lys Pro Phe Val Phe
1               5                   10
```

(2) INFORMATION FOR SEQ ID NO:8:

(i) SEQUENCE CHARACTERISTICS:
    (A) LENGTH: 29 amino acids
    (B) TYPE: amino acid
    (D) TOPOLOGY: linear (ii) MOLECULE TYPE: peptide (iii) HYPOTHETICAL: NO (vi) ORIGINAL SOURCE:
    (A) ORGANISM: Homo sapiens (xi) SEQUENCE DESCRIPTION: SEQ ID NO:8:

```
    Val  Ile  Pro  Pro  Glu  Val  Lys  Phe  Asn  Lys  Pro  Phe  Val  Phe  Leu  Met
    1              5                        10                      15

Ile  Asp  Gln  Asn  Thr  Lys  Val  Pro  Leu  Phe  Met  Gly  Lys
                   20                  25
```

( 2 ) INFORMATION FOR SEQ ID NO:9:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:9:

```
    Met  Ile  Pro  Pro  Glu  Val  Lys  Phe  Asn  Lys  Pro  Phe  Val  Phe  Leu  Met
    1              5                        10                      15

Ile  Asp  Gln  Asn  Thr  Lys  Cys  Pro  Cys  Phe  Met  Gly  Cys
                   20                  25
```

( 2 ) INFORMATION FOR SEQ ID NO:10:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:10:

```
    Val  Ile  Pro  Pro  Glu  Val  Lys  Phe  Asn  Lys  Pro  Phe  Val  Phe  Leu  Met
    1              5                        10                      15

Ile  Asp  Gln  Asn  Thr  Lys  Cys  Pro  Leu  Phe  Met  Gly  Lys
                   20                  25
```

( 2 ) INFORMATION FOR SEQ ID NO:11:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:11:

```
    Val  Ile  Pro  Pro  Glu  Val  Lys  Phe  Asn  Cys  Pro  Phe  Val  Phe  Leu  Met
    1              5                        10                      15

Ile  Asp  Gln  Asn  Thr  Lys  Val  Pro  Leu  Phe  Met  Gly  Lys
                   20                  25
```

( 2 ) INFORMATION FOR SEQ ID NO:12:

( i ) SEQUENCE CHARACTERISTICS:
        ( A ) LENGTH: 29 amino acids (B) TYPE: amino acid
(D) TOPOLOGY: linear (ii) MOLECULE TYPE: peptide (iii) HYPOTHETICAL: NO (vi) ORIGINAL SOURCE:
(A) ORGANISM: Homo sapiens (xi) SEQUENCE DESCRIPTION: SEQ ID NO:12:

Val Ile Pro Pro Glu Val Lys Phe Asn Lys Pro Phe Val Phe Leu Met
1               5                   10                  15
Ile Asp Gln Asn Thr Lys Thr Pro Leu Phe Met Gly Lys
            20                  25

(2) INFORMATION FOR SEQ ID NO:13:

(i) SEQUENCE CHARACTERISTICS:
(A) LENGTH: 29 amino acids
(B) TYPE: amino acid
(D) TOPOLOGY: linear (ii) MOLECULE TYPE: peptide (iii) HYPOTHETICAL: NO (vi) ORIGINAL SOURCE:
(A) ORGANISM: Homo sapiens (xi) SEQUENCE DESCRIPTION: SEQ ID NO:13:

Met Ile Pro Pro Glu Val Lys Phe Asn Lys Pro Phe Val Phe Leu Met
1               5                   10                  15
Ile Asp Gln Asn Thr Lys Cys Cys Leu Phe Met Gly Lys
            20                  25

(2) INFORMATION FOR SEQ ID NO:14:

(i) SEQUENCE CHARACTERISTICS:
(A) LENGTH: 29 amino acids
(B) TYPE: amino acid
(D) TOPOLOGY: linear (ii) MOLECULE TYPE: peptide (iii) HYPOTHETICAL: NO (vi) ORIGINAL SOURCE:
(A) ORGANISM: Homo sapiens (xi) SEQUENCE DESCRIPTION: SEQ ID NO:14:

Arg Ile Pro Pro Glu Val Lys Phe Asn Lys Pro Phe Val Phe Leu Met
1               5                   10                  15
Ile Asp Gln Asn Thr Lys Arg Pro Leu Phe Met Gly Lys
            20                  25

(2) INFORMATION FOR SEQ ID NO:15:

(i) SEQUENCE CHARACTERISTICS:
(A) LENGTH: 29 amino acids
(B) TYPE: amino acid
(D) TOPOLOGY: linear (ii) MOLECULE TYPE: peptide (iii) HYPOTHETICAL: NO (vi) ORIGINAL SOURCE:
(A) ORGANISM: Homo sapiens (xi) SEQUENCE DESCRIPTION: SEQ ID NO:15:

```
   Arg  Ile  Pro  Pro  Glu  Val  Lys  Phe  Asn  Lys  Pro  Phe  Val  Phe  Leu  Met
   1              5                        10                       15

Ile  Asp  Gln  Asn  Thr  Lys  Cys  Pro  Cys  Phe  Met  Gly  Cys
                  20                       25
```

( 2 ) INFORMATION FOR SEQ ID NO:16:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:16:

```
   Arg  Ile  Pro  Pro  Glu  Val  Lys  Phe  Asn  Lys  Pro  Phe  Val  Phe  Leu  Met
   1              5                        10                       15

Ile  Asp  Gln  Asn  Thr  Lys  Cys  Pro  Cys  Phe  Met  Gly  Cys  Val  Val  Asn
                  20                       25                       30

Cys  Thr  Glu
                  35
```

( 2 ) INFORMATION FOR SEQ ID NO:17:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:17:

```
   Val  Ile  Pro  Pro  Glu  Val  Lys  Phe  Asn  Lys  Pro  Phe  Val  Phe  Leu  Met
   1              5                        10                       15

Ile  Glu  Gln  Asn  Thr  Lys  Ser  Pro  Leu  Phe  Met  Gly  Lys
                  20                       25
```

( 2 ) INFORMATION FOR SEQ ID NO:18:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:18:

```
   Val  Ile  Pro  Pro  Glu  Val  Lys  Phe  Asn  Lys  Pro  Phe  Val  Phe  Leu  Met
   1              5                        10                       15

Ile  Glu  Gln  Asn  Thr  Lys  Ser  Pro  Leu  Phe  Met  Gly  Lys  Val  Val  Asn
                  20                       25                       30

Pro  Thr  Gln
```

(2) INFORMATION FOR SEQ ID NO:19:

(i) SEQUENCE CHARACTERISTICS:
    (A) LENGTH: 35 amino acids
    (B) TYPE: amino acid
    (D) TOPOLOGY: linear (ii) MOLECULE TYPE: peptide (iii) HYPOTHETICAL: NO (vi) ORIGINAL SOURCE:
    (A) ORGANISM: Homo sapiens (xi) SEQUENCE DESCRIPTION: SEQ ID NO:19:

```
Ser  Ile  Pro  Pro  Glu  Val  Lys  Phe  Asn  Lys  Pro  Phe  Val  Phe  Leu  Met
 1                   5                        10                       15

Ile  Glu  Gln  Asn  Thr  Lys  Ser  Pro  Leu  Phe  Met  Gly  Lys  Val  Val  Asn
                20                        25                       30

Pro  Thr  Gln
           35
```

IMMUNOCHEMICAL ASSAYS FOR CANCER-ASSOCIATED SCM-RECOGNITION FACTOR

CROSS REFERENCES

This is a continuation of application Ser. No. 07/927,534 filed on Aug. 10, 1992, abandoned, which is a continuation-in-part of application Ser. No. 07/539,686, filed Jun. 18, 1990, and entitled "Cancer-Associated SCM-Recognition Factor, Preparation and Method of Use," which is a continuation-in-part of Ser. No. 07/167,007, filed Mar. 11, 1988, entitled "General Cancer-Associated SCM-Recognition Factor, Preparation and Method of Use," and now abandoned, which itself was a continuation-in-part of Ser. No. 07/022,759, filed Mar. 6, 1987, also entitled "General Cancer-Associated SCM-Recognition Factor, Preparation and Method of Use," and also now abandoned. All of these applications are by Dr. Boris Cercek and Dr. Lea Cercek, and are incorporated herein by this reference. This application is also related to several prior patent applications, all by Drs. Boris & Lea Cercek: (1) Ser. No. 06/838,264, filed Mar. 10, 1986 (now abandoned), and Ser. No. 07/260,928, filed Oct. 21, 1988, a continuation-in-part of Ser. No. 06/838,264, both entitled "Provision of Density Specific Blood Cells for the Structuredness of the Cytoplasmic Matrix (SCM) Test"; and (2) Ser. No. 06/867,079, filed May 27, 1986 (now abandoned), and Ser. No. 07/222,115, filed Jul. 20, 1988, a continuation-in-part of Ser. No. 06/867,079, both entitled "Method for Measuring Polarization of Bathochromically Shifted Fluorescence." The disclosures of these related patent applications are incorporated herein by this reference.

BACKGROUND

Many diseases occurring in humans and animals can be detected by the presence of foreign substances, particularly in the blood, the substances being specifically associated with a disease or condition. Tests for antigens or other such substances produced as a result of such diseases show great promise as a diagnostic tool for the early detection of the particular disease which produced the antigen or other substance. Procedures for the detection of such substances must be reliable, reproducible, and sensitive in order to constitute a practical diagnostic procedure for health care providers. In addition, any such procedure should be able to be carried out quickly and inexpensively by persons of ordinary skill and training in laboratory procedures.

For example, in the treatment of the various malignancies that afflict humans and animals, referred to generally as cancer, it is recognized that early detection is the key to effective treatment, especially as most therapeutic procedures are more effective and safer in relatively early stages of cancer than in later stages. For example, many chemotherapeutic drugs that are toxic to malignant cells are also toxic to normal cells, and the higher doses required to cure or arrest more advanced cases of cancer can cause uncomfortable and serious side effects. Also, surgery is most often effective only before the disease has spread or metastasized. Far too many cases of cancer are only discovered too late for effective treatment.

Accordingly, there has been and continues to be a great need for reliable tests that can diagnose cancer at early stages, and a great deal of research effort has gone to this end. In this connection new tests and procedures are being developed to effect early diagnosis of cancer.

One extremely desirable aspect of such a test is its ability either to detect all types of cancer generally, and once the cancer is detected, identify the specific type of cancer, depending on the materials used. The former application of such a test is very important in mass screenings of large patient populations, as would be done in routine checkups. In such mass screenings a test dependent on a particular type of cancer would not be desirable, as there are literally hundreds, if not thousands, of types of cancer and a test that could spot only one or a few types of the disease is far too likely to miss many cases of cancer. In general, these patients would present either no symptoms or vague generalized symptoms that could not be readily linked to a particular type of cancer, so there would be no basis for suspecting a particular type and administering a test specific for that type.

In contrast, once the presence of malignancy is known or strongly suspected, it would be desirable to have a test that could pinpoint the particular type of malignancy present. Such a test could add greatly to the efficiency of treatment, because many of the most effective cancer therapies, such as chemotherapeutic agents, are only effective against one type of cancer or at best, a narrow range of types, and the wrong chemotherapy can do more harm than good.

In an effort to meet this need and to improve the diagnosis and early detection of cancer in human and animal bodies, a test procedure has been developed which involves the measurement of changes in the structuredness of the cytoplasmic matrix (SCM) of living lymphocytes when exposed either to phytohaemagglutinin or to cancer-associated antigens. This procedure has been described in L. Cercek, B. Cercek, and C. I. V. Franklin, "Biophysical Differentiation Between Lymphocytes from Healthy Donors, Patients with Malignant Diseases and Other Disorders," *Brit J. Cancer* 29, 345–352 (1974), and L. Cercek and B. Cercek, "Application of the Phenomenon of Changes in the Structuredness of Cytoplasmic Matrix (SCM) in the Diagnosis of Malignant Disorders: a Review," *Europ. J. Cancer* 13, 903–915 (1977).

In accordance with this procedure, a subpopulation of potentially SCM-responding lymphocytes is separated from a blood sample of the patient being tested and the lymphocytes are incubated with malignant tissue or extracts of malignant tissue. If the blood sample donor is afflicted with a malignancy, there is a characteristic SCM response that can be differentiated from the SCM response of lymphocytes from donors not afflicted with a malignancy. The SCM response is determined by measuring changes in intracellular fluorescein fluorescence polarization of the SCM-responding lymphocytes.

The changes seen in the SCM test are believed to reflect changes in the internal structure of the lymphocyte as the lymphocyte is activated for synthesis. These changes are seen as a decrease in the fluorescence polarization of the cells when polarized light is used to excite the fluorescein present in the cells. Fluorescence polarization is a measure of intracellular rigidity; the greater the intracellular mobility, the less the measured fluorescence polarization. An observed decrease in fluorescence polarization is thought to result mainly from changes in the conformation of the mitochondria, the energy-producing organelles of the cell. The change in the mitochondria is believed to result from the contractions of the cristae or inner folds of the mitochondrial membrane. The SCM reflects the forces of interaction between macromolecules and small molecules such as water molecules, ions, adenosine triphosphate, and cyclic adenosine phosphate. Perturbations of these interactions result in changes in the SCM.

The SCM test is capable of responding to a relatively small quantity of malignant cells. About $10^9$ cells in a person weighing 70 kg are enough to cause the lymphocytes to respond in the SCM test in the characteristic pattern of malignancy. In mice, when as few as $3.5 \times 10^5$ Ehrlich ascites (tumor) cells are implanted, the pattern of the response in the SCM test is altered; response to cancer-specific antigens is induced, while the normal response to phytohaemagglutinin is virtually eliminated (L. Cercek and B. Cercek, "Changes in SCM-Responses of Lymphocytes in Mice After Implantation with Ehrlich Ascites Cells," *Europ. J. Cancer* 17, 167–171 (1981)).

The SCM test allows early detection of cancer, often much earlier than is possible by conventional methods, with relatively little discomfort to the patient except as may be involved in taking a blood sample.

However, this procedure does have disadvantages. For example, it requires preparation of crude extracts from tumor tissues and the like or the use of the tumor tissue itself as a source of cancer-associated antigens. There are several major problems with the use of malignant tissue or extracts of such tissue in the SCM test. For example, it is sometimes difficult to obtain the required quantity of tissue. Also, the use of whole tissues or crude extracts of tissues can introduce interfering substances into the test procedure. These interfering substances can adversely affect the sensitivity of the test or adversely affect the test results themselves. The presence or absence of these interfering substances can easily vary from batch to batch of malignant tissue, introducing undesirable variability into the SCM test. Additionally, because the interfering substances are present in whole tissue or crude extracts, they are very difficult to identify or quantitate.

Additionally, as disclosed in U.S. patent application Ser. No. 07/539,686, there exists at least partial homology between the SCM factors occurring in vivo and portions of proteins associated with inflammation, especially the glycoprotein $\alpha_1$-protease inhibitor ($\alpha_1$-PI). Although inflammation does not give false positive results in the fluorescence polarization-based SCM test, it would be desirable to develop an immunoassay that could give results equivalent to the SCM test and would be simpler to perform and would require less equipment. Accordingly, there exists a need for a sensitive, reliable immunoassay that can detect SCM factor in body fluids such as blood or plasma, either in the presence or the absence of partially homologous inflammation-associated proteins.

SUMMARY

We have developed antibodies specific for the SCM cancer-recognition factor, as well as immunoassays that can detect SCM factor in samples in the presence of partially-homologous peptide sequences. These partially-homologous sequences can include portions of inflammation-associated proteins such as $\alpha_1$-protease inhibitor ($\alpha_1$-PI). The samples for which such assays can be used include both cellular samples and samples comprised of substantially cell-free body fluids, as well as culture media or other aqueous fractions that may contain SCM factor.

In general, such an immunoassay comprises:

(1) incubating a first aliquot of the sample with a first antibody specific for the cancer-recognition factor to bind the first antibody to the cancer-recognition factor and to the partially homologous peptide sequence in the first aliquot;

(2) incubating a second aliquot of the sample with a second antibody specific for a portion of the partially homologous peptide sequence lacking any substantial homology with any portion of the sequence of the cancer-recognition factor to bind the second antibody only to the partially homologous peptide sequence in the second aliquot; and (3) comparing the quantity of the first antibody bound to the first aliquot with the quantity of the second antibody bound to the second aliquot to detect the cancer recognition factor.

In this assay, the step of comparing the quantity of the first antibody bound to the first aliquot to the quantity of the second antibody bound to the second aliquot typically comprises:

(i) reacting the incubated aliquots of steps (1) and (2) separately with a detection antibody specific for both the first and second antibodies, the detection antibody being coupled to a detectable label; and (ii) detecting the label.

Alternatively, the first and second antibodies are each coupled to, e.g., a member of the avidin-biotin specific binding pair, the first and second antibodies being coupled to the same binding pair member. In this alternative, the step of comparing the quantity of the first antibody bound to the first aliquot with the quantity of the second antibody bound to the second aliquot comprises:

(i) reacting the incubated first and second aliquot separately with a detectable label, the detectable label being coupled to the specific binding pair member complementary to the specific binding pair member that is coupled to the first and second antibody; and (ii) separately detecting the label bound to the first and second aliquots in order to determine the presence of the SCM factor.

Preferably, the sample is a cellular sample.

The partially homologous peptide sequence is typically $\alpha_1$-PI (also known as $\alpha_1$-antitrypsin), the sequence of whose carboxy-terminal region is substantially homologous with the sequences of known SCM-active cancer-recognition factors. The amino-terminal portion of $\alpha_1$-PI lacks substantial homology with any portion of the SCM-active cancer-recognition factors.

When the sample in which SCM factor to be detected is a cellular sample, and the partially homologous peptide sequence is the carboxy-terminal portion of $\alpha_1$-PI, a preferred version of the immunoassay comprises the steps of:

(1) incubating a first aliquot of the cells with a first rabbit IgG antibody specific for the cancer recognition factor to bind the first antibody to the cells of the first aliquot, the first antibody being selected from the group consisting of: (i) an antibody produced by immunization with the peptide M-I-P-P-E-V-K-F-N-K-P-F-V-F-L-M-I-D-Q-N-T-K-V-P-L-F-M-G-K-C (SEQ ID NO: 1) conjugated at its carboxy-terminal cysteine residue to a carrier protein; and (ii) an antibody produced by immunization with the peptide M-I-P-P-E-V-K-F-N-K-P-F-V-F-L-M-I-D-Q-N-T-K-V-P-L-F-M-G-K (SEQ ID NO: 2), the first antibody binding both to the cancer-recognition factor and the $\alpha_1$-PI in the first aliquot;

(2) incubating a second aliquot of the cells with a second rabbit IgG antibody specific for the amino-terminal 19 amino acid sequence of $\alpha_1$-PI, the amino-terminal 19 amino acid sequence of $\alpha_1$-PI lacking any substantial homology with any portion of the sequence of the cancer-recognition factor, the second antibody binding only to the $\alpha_1$-PI in the second aliquot;

(3) reacting the incubated aliquots of steps (1) and (2) separately, each incubated aliquot being reacted with an antibody specific for rabbit IgG antibody coupled to an enzyme label to label the first antibody bound to the first aliquot and the second antibody bound to the second aliquot;

(4) incubating the bound enzyme-labeled antibodies of the first and second aliquots separately, each with an indicator that yields a detectable product in response to enzymatic activity of the enzyme; and (5) comparing the quantity of detectable product produced by the first and second aliquots to detect the cancer-recognition factor.

Another aspect of the invention is a method for determining the content of cancer-recognition factor in a body fluid comprising the steps of:

(1) mixing the body fluid and an antibody specific for cancer-recognition factor as described above; and (2) determining the extent of reaction between the cancer-recognition factor in the body fluid and the antibody by performing an immunoassay.

The immunoassay can be a radioimmunoassay, a fluorescence immunoassay, a chemiluminescence immunoassay, or an enzyme-linked immunoassays.

In one preferred embodiment of the method, the method is an enzyme-linked immunoassay comprising:

(1) attaching the cancer-recognition factor or an immunologically equivalent analog thereof to a solid phase capable of binding protein;

(2) adding the body fluid to the solid phase;

(3) incubating the solid phase with a first antibody specific for the cancer-recognition factor;

(4) incubating the solid phase with a second antibody that is specific for the first antibody, the second antibody being labeled with an enzyme producing a colorimetrically detectable product when the enzyme is incubated with a substrate;

(5) adding the substrate for the enzyme; and (6) measuring the absorbance of the colorimetrically detectable product.

Another aspect of the invention is antibodies specifically binding a cancer-recognition factor and useful in the immunoassays discussed above. In general, the factor bound by these antibodies is a peptide of at least 9 amino acid residues, including a core sequence of 9 amino acid residues, the core sequence being $F-X_{15}-M-X_{17}-X_{18}-X_{19}-X_{20}-X_{21}-K$. In the core sequence, $X_{15}$ and $X_{17}$ are each independently selected from the group consisting of I, L, and V; $X_{18}$ is selected from the group consisting of D and E; $X_{19}$ and $X_{20}$ are each independently selected from the group consisting of Q and N, and $X_{21}$ is selected from the group consisting of S and T. The factor is capable of producing at least a 10% decrease of the intracellular fluorescence polarization value of lymphocytes capable of responding in the structuredness of the cytoplasmic matrix (SCM) test isolated from donors afflicted with cancer. Particularly preferred cancer-recognition factors bound by the antibody have 9, 15 or 22 amino acid residues representing fragments of the synthetic SCM.

Alternatively, the antibody specifically binds a peptide selected from the group consisting of M-I-P-P-E-V-K-F-N-K-P-F-V-F-L-M-I-D-Q-N-T-K-V-P-L-F-M-G-K (SEQ ID NO: 2) and a peptide related thereto by one or more conservative amino acid substitutions.

As another alternative, the antibody specifically binds a cancer-recognition factor of 29 amino acid residues. The cancer-recognition factor bound by the antibody has an amino acid sequence of $M-X_2-P-P-X_5-X_6-K-F-X_9-K-P-F-X_{13}-F-X_{15}-M-X_{17}-X_{18}-X_{19}-X_{20}-X_{21}-K-X_{23}-P-X_{25}-F-M-G-K$, wherein $X_2$, $X_6$, $X_{13}$, $X_{15}$, $X_{17}$, $X_{23}$, and $X_{25}$ are each independently selected from the group consisting of I, L, and V; $X_5$ and $X_{18}$ are each independently selected from the group consisting of D and E; $X_9$, $X_{19}$, and $X_{20}$ are each independently selected from the group consisting of Q and N, and $X_{21}$ is selected from the group consisting of S and T.

As another alternative, the antibody specifically binds a cancer-recognition factor of from 29 to 35 amino acid residues in length, including a core sequence at amino acids 14–22 of $F-L-M-I-X_{18}-Q-N-T-K$, wherein $X_{18}$ is selected from the group consisting of D and E.

Particularly preferred antibodies are: (1) an antibody specific for a cancer recognition factor prepared by immunization of an antibody-producing animal with a peptide M-I-P-P-E-V-K-F-N-K-P-F-V-F-L-I-M-I-D-Q-N-T-K-V-P-L-F-M-G-K-C (SEQ ID NO: 1) conjugated at its carboxy-terminal cysteine residue to a carrier protein; and (2) an antibody specific for a cancer-recognition factor prepared by immunizing a antibody-producing animal with a peptide M-I-P-P-E-V-K-F-N-K-P-F-V-F-L-M-I-D-Q-N-T-K-V-P-L-F-M-G-K (SEQ ID NO: 2).

DRAWINGS

These and other features, aspects, and advantages of the present invention will become better understood with reference to the following description, appended claims, and the accompanying drawings where:

FIG. 1 is a schematic depiction of one form of ELISA assay for the SCM factor;

Figure 3:
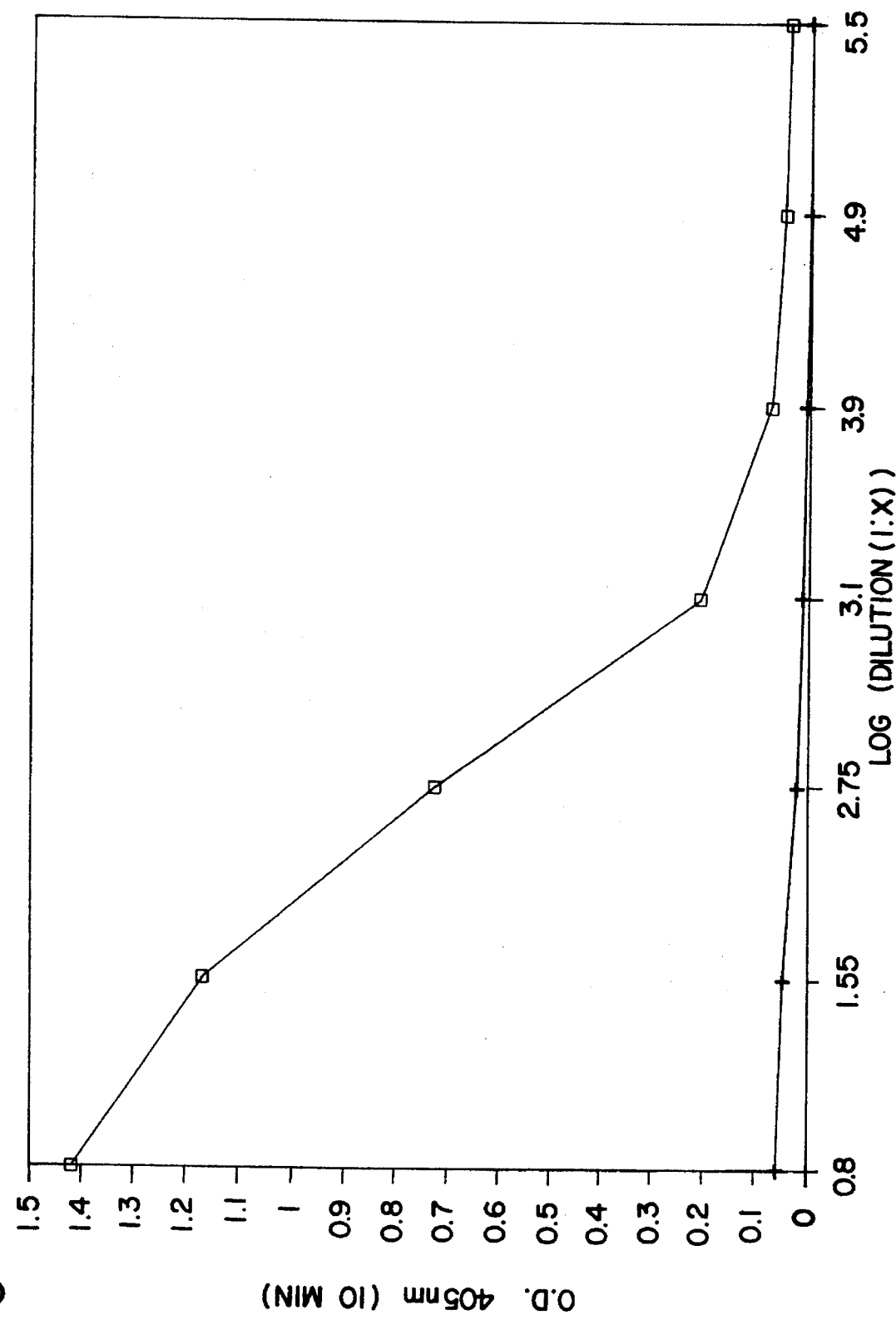
Figure 4:
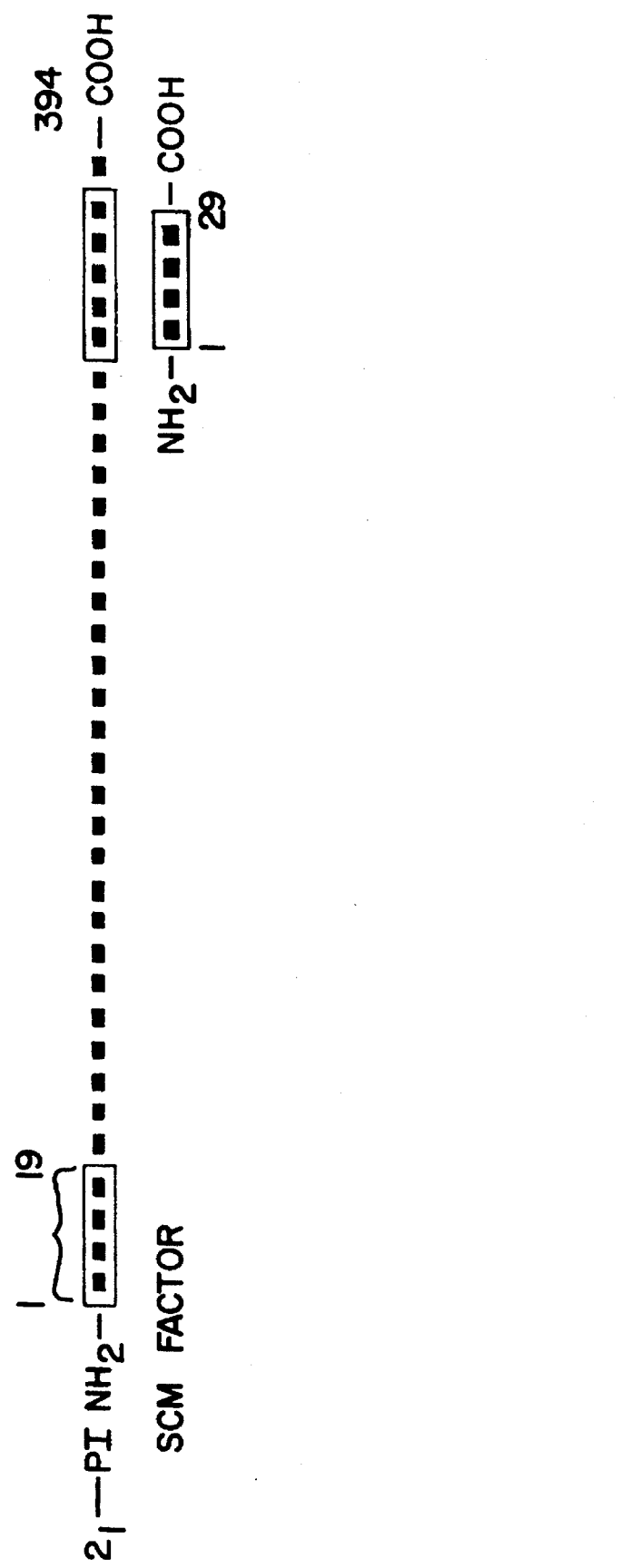

FIG. 3 shows the results obtained from an experiment in which the reactivity of antiserum raised against SCM factor conjugated with keyhole limpet hemocyanin (KLH), as determined by absorbance at 405 nm in a version of the ELISA assay, was measured as a function of the dilution of the antiserum; and FIG. 4 is a schematic depiction of the two-analyte immunoassay of the present invention, showing the amino acid sequences bound by the first antibody that binds both the SCM factor and the partially homologous peptide sequence and the second antibody that binds only partially homologous peptide sequence.

DEFINITIONS

Definitions for a number of terms which are used in the following Description, Examples, and appended claims are collected here for convenience.

"General": Nonspecific with respect to the particular type of cancer afflicting either the donor of the body fluid from which the SCM factor of the present invention is purified, or the donor of the lymphocytes used with that factor in the SCM test.

"Fluorogenic Agent Precursor": A nonfluorogenic compound capable of being taken up by lymphocytes and converted intracellularly by hydrolysis into a fluorogenic compound, of which the example used herein is fluorescein diacetate (FDA).

"Standard SCM Test": An SCM test using 1.0 ml of a lymphocyte suspension at $6 \times 10^6$ cells/ml and 0.1 ml of the cancer recognition factor or mitogen, with FDA as the fluorogenic agent precursor and using an excitation wavelength of 470 nm and an emission wavelength of 510 nm for fluorescence polarization measurements.

"Apparent Molecular Weight" and "Nominal Molecular Weight Cutoff": Both of these terms refer to the fact that the separation of molecules by ultrafiltration according to size is approximate for molecules in the size range of SCM factor, and depends on conformation as well as size. Thus an ultrafilter with a nominal molecular weight cutoff of x daltons will separate molecules with an apparent molecular weight of less than x daltons from molecules with an apparent molecular weight greater than x daltons. However, some molecules with an actual molecular weight greater than x daltons will pass through such a filter.

"Substantially Pure Cancer Recognition Factor": Material exhibiting cancer recognition activity as determined in the SCM test and of such a state of purity that at least about 95% of other molecules with specific biological activity, including all proteins and larger peptides, is not present in the material. The term "substantially purified" refers to the same state of purity.

"Tryptic Peptide": A peptide cleaved from a larger peptide by the action of the proteolytic enzyme trypsin, which breaks peptide chains after lysine or arginine residues.

"Partially Homologous": Two peptide or protein sequences are partially homologous when there exists a degree of residue-to residue correspondence between the two sequence greater than about 40%, i.e., substantially greater than expected by chance.

DESCRIPTION

This invention relates to our preparation of antibodies capable of specifically binding cancer-associated SCM-recognition factors and use of such antibodies in immunoassays to detect the factors, including immunoassays that can detect the factors in the presence of partially homologous peptide sequences. Such partially homologous peptide sequences can include the carboxyl-terminal portion of the inflammation-related protein $\alpha_1$-protease inhibitor ($\alpha_1$-PI).

We previously isolated twelve peptides that are general cancer-associated SCM-recognition factors from sera isolated from a number of patients from different types of cancer. These peptides are all between 29 and 35 amino acids in length, cross-react in the SCM test, and show a striking homology in amino acid sequence. This homology is so striking that a 29-amino acid peptide representing a consensus sequence of the twelve purified peptides was synthesized. This peptide, designated as "synthetic SCM factor", has the amino acid sequence M-I-P-P-E-V-K-F-N-K-P-F-V-F-L-M-I-D-Q-N-T-K-V-P-L-F-M-G-K (SEQ ID NO: 2). This synthetic peptide shares all of the properties of the general cancer-associated SCM-recognition factor isolated from the blood plasma of cancer patients, including activity in the SCM test and immunochemical reactivity. Even more unexpectedly, a region of nine amino acids within that sequence, amino acids 14–22, with the sequence F-L-M-I-D-Q-N-T-K (SEQ ID NO: 3), is equally active in the SCM test. Other partial sequences, including amino acids 8–22, 8–29, and 1–22, that incorporate the 14–22 sequence are also fully active. The antibodies that we have prepared take advantage of the conservation of structure within the SCM-factor peptides and the activity of domains within the peptides to provide immunochemical assays of high specificity for the factors.

Biological properties of both the natural purified and the synthetic SCM factors were previously described, e.g., in U.S. patent application Ser. No. 07/539,686, incorporated by reference. These properties are substantially identical, as far as has been determined, for the natural and synthetic SCM factors, and include: (1) the ability of the SCM factor to modify the SCM responses of lymphocytes from donors free of malignancy; (2) cross-reactivity of the factor isolated from donors with various types of cancer in the SCM test; (3) its ability to suppress the in vitro natural cytotoxicity of killer lymphocytes toward malignant cells; and (4) the newly discovered property of the SCM factor of protecting proteases that are believed to aid in the proliferation and invasion of cancer cells from inhibition by the natural inhibitor of those proteases, $\alpha_1$-PI.

Additionally, we have unexpectedly discovered that the SCM-factors are partially homologous to the carboxyl-terminal region of $\alpha_1$-PI, and have developed a two-analyte immunoassay to allow the immunoassay of SCM-factors in the presence of $\alpha_1$-PI. Such a two-analyte immunoassay can detect the SCM factors in the presence of cellular $\alpha_1$-PI molecules, which contain in their carboxy-terminal portion an amino acid sequence partially homologous to the amino acid sequence of the SCM-factor peptides. For this purpose, antibodies were raised against the SCM-factor peptide (first antibody) and against a amino-terminal 19 residue segment of the $\alpha_1$-PI protein, a region lacking substantial homology with any portion of the SCM-factor peptide molecule (second antibody). Hence, this two-analyte assay can detect the presence of the SCM-factor peptide in samples containing both the SCM factor peptide and cellular $\alpha_1$-PI.

I. ISOLATED AND PURIFIED GENERAL CANCER-ASSOCIATED SCM-RECOGNITION FACTORS

The general cancer-associated SCM-recognition factor was isolated and purified to homogeneity from blood plasma obtained from patients with twelve different types of cancer. As detailed below, these peptides all are either 29 or 35 amino acids in length and are substantially homologous in amino acid sequence.

A. Purification

The purification of the SCM-recognition factor to substantial homogeneity from blood plasma was performed as described in U.S. patent application Ser. No. 07/167,007 by Drs. Boris and Lea Cercek, entitled "General Cancer-associated SCM-recognition Factor, Preparation and Method of Use" and incorporated herein by this reference. The purification process preferably occurs in five steps: (1) ultrafiltration; (2) desalting; (3) gel filtration; (4) anion-exchange chromatography; and (5) reverse-phase high-pressure liquid chromatography (RP-HPLC).

1. Ultrafiltration

The first step in purification of the SCM factor is obtaining an ultrafiltrate from a body fluid of a donor afflicted with cancer. The body fluid can be peripheral blood, blood plasma, or urine; if the fluid is peripheral blood, the blood is centrifuged to separate the red blood cells from the plasma. The donor of the body fluid used for isolation of the SCM factor can be either autologous or allogeneic with respect to the lymphocytes used for the SCM test. Alternatively, the SCM factor can be purified from cell aspirates or other cellular materials derived from patients with malignancies.

The ultrafiltration process separates the first fraction of the body fluid comprising molecules having an apparent molecular weight greater than 1,000 daltons from a second fraction comprising molecules having an apparent molecular weight less than 1,000 daltons. The general cancer-associated SCM factor of the present invention is found in the second fraction of the ultrafiltrate. The terms "apparent molecular weight" and "nominal molecular weight cutoff" are used herein because ultrafiltration is a somewhat imprecise method of separating molecules according to molecular weight in this molecular weight range, and the exact molecular weight excluded by a filter with a nominal molecular weight cutoff of 1,000 daltons depends somewhat on the conformation of the molecule. Molecules larger than 1,000 daltons in actual molecular weight can, in fact, pass through an ultrafilter with a nominal molecular weight cutoff of 1,000 daltons if, for example, the molecules are relatively long and narrow. In fact, the purified general cancer-associated SCM factors of the present invention are either 29 or 35 amino acids long and have molecular weights of approximately 3,200 or 4,000 daltons, respectively. Nevertheless, all of these peptides pass through an ultrafilter with a nominal molecular weight cutoff of 1,000 daltons.

Preferably, the separation of the second fraction from the first fraction is performed by filtration of the body fluid through an ultrafilter with a nominal 1,000-dalton molecular weight cutoff, such as, but not limited to, an AMICON™ UM2 or YM2 filter (available from Amicon Corporation, Scientific System Division, Danvers, Mass. 01923).

The purity of a preparation of such a factor, at the ultrafiltrate stage or later, can be described by its specific activity. In this context, the term "specific activity" is defined as the reciprocal of the quantity of protein required to cause a particular degree of decrease, such as 20%, in the intracellular fluorescence polarization value when a particular fraction is used to challenge SCM-responding lymphocytes in the SCM test. The goal of purification of the SCM factor is to increase the specific activity of the SCM factor over the specific activity found in the crude ultrafiltrate. The process of purification can therefore be followed by determining the specific activity of the purified fractions at each stage. Since the protein concentration in the examples reported herein is only determined approximately in terms of ultraviolet absorbance, preferably at 220 nm, and the complete dose-response curve for the factor has not yet been determined, the characterization of various steps of the purification of the SCM factor described herein in terms of specific activity is only approximate. However, it is clear that the protein concentration decreases markedly as the factor moves through the various purification steps while the activity of the factor is relatively unaffected, thereby resulting in an increase in specific activity of the SCM factor. Nevertheless, even the ultrafiltrate can properly be described as consisting essentially of substantially purified general cancer-associated SCM-recognition factor, inasmuch as ultrafiltration through a membrane with a nominal molecular weight cutoff of 1,000 daltons removes from a biological fluid the overwhelming majority of molecules with any biological activity, including all proteins and larger peptides.

2. Desalting

The next step in the purification of the general cancer-associated SCM factor is a desalting step in which the fraction obtained from ultrafiltration is loaded on a chromatographic column capable of separating the salts therefrom. The material loaded onto the column is then eluted from the column with distilled water, and the portion eluting at an elution volume of between about 0.3 and about 0.5 times the total chromatographic bed volume, containing the SCM factor, is collected. Preferably, the column used in this step is a gel-filtration column with a fractionation range of from 0 to about 700 daltons, such as SEPHADEX™ G-10 (Pharmacia, Uppsala, Sweden), a dextran gel. A polyacrylamide gel with corresponding separation characteristics can also be used.

3. Gel Filtration

The next step in the purification is another gel filtration step, again separating according to size. The SCM-containing material obtained from the desalting step is loaded onto another gel filtration column with a fractionation range of from about 1,500 to about 30,000 daltons. Preferably, the gel filtration column material is a dextran such as SEPHADEX™ G-50, but a corresponding polyacrylamide gel can also be used. The material loaded onto the column is then eluted therefrom with a weak aqueous solution of an ammonium salt. Preferably, the ammonium salt is ammonium bicarbonate, more preferably 50 mM ammonium bicarbonate. That portion eluting at an elution volume between about 0.4 times and about 0.6 times the total chromatographic bed volume contains the SCM factor and is collected.

4. Anion-exchange Chromatography

The next step in the purification is an anion-exchange chromatography step, separating by charge. The SCM factor-containing material from the previous gel filtration step is loaded onto an anion exchange column, preferably diethylaminoethyl-cellulose (DEAE-cellulose). The material loaded onto the column is then eluted therefrom with an increasing concentration of an ammonium salt. Preferably, the ammonium salt is ammonium bicarbonate and the increasing concentration of the ammonium salt is from 10 mM to 1.0M ammonium bicarbonate. The fraction eluting from the column at about 0.28M to 0.31M ammonium bicarbonate contains the SCM factor and is collected.

5. Reverse-phase High-pressure Liquid Chromatography

The final step of purification is reverse-phase high-pressure liquid chromatography (RP-HPLC), which separates by charge and/or hydrophobicity. Typically, the SCM factor-containing material from the DEAE-cellulose column eluate is loaded onto an AQUAPORE™ RP-300 RP-HPLC column with dimensions of 220 mm×2.1 mm. Elution is then performed with a combination of two solvents: initially, 90 volume percent of 0.1 volume percent aqueous trifluoroacetic acid (TFA) (solvent A) and 10 volume percent of 0.09 volume percent of TFA in aqueous 70% acetonitrile (solvent B), followed by a gradient with an increasing concentration of solvent B. The SCM factor from all starting materials elutes as an homogeneous peak at a solvent composition of 26 volume percent solvent A and 74 volume percent solvent B.

Alternatively, RP-HPLC can be performed on a Beckman Instruments Ultrasphere ODS™ column. With this column, elution is then performed with a somewhat different solvent pattern, initially 70 volume percent of solvent A and 30 volume percent of 0.1 volume percent aqueous TFA in aqueous 70% acetonitrile (solvent C), followed by a gradient with an increasing concentration of solvent C. The SCM factor always elutes as an homogeneous peak at a solvent composition of 43.7 volume percent of solvent A and 56.3 volume percent of solvent C when the Ultrasphere column and this solvent system is used.

B. Structure of the Isolated Cancer-associated SCM-recognition Factor

The amino acid sequences of the SCM factors isolated from blood plasmas from patients with 12 different types of cancer have been determined by sequential Edman degradation. The results are reported in Example 6, below. Certain residues are unidentified; these residues are likely cysteine and are reported herein as such. In nine out of the twelve cancers, the SCM factor was 29 amino acids long; in the remaining three, an additional six amino acids were present, yielding a total of 35 amino acids. In seven of twelve of the factor preparations, polymorphisms exist, in that there are conservative substitutions at one or two positions of the peptide. Also, in two cases, gastric sarcoma and prostate cancer, the SCM factor appears in two forms, one of 29 amino acid residues and the other of 35 amino acid residues. For seminoma of the testes, only the 35 amino acid form is found. No forms of intermediate length are found in these samples. However, several intermediate length peptides are possible, even some peptides shorter than 29 amino acids, due to truncation or the existence of mutant forms. These slight differences in amino acid sequence do not affect the cross-reactivity of the factors in the SCM test.

One region of the sequence is nearly invariant —residues 14–22. This sequence is F-L-M-I-D-Q-N-T-K (SEQ ID NO: 3), except in the factors for prostate cancer and seminoma of the testes, in which E (glutamate) replaces D (aspartate) at position 18. This change is extremely conservative, inasmuch as glutamate and aspartate have the same charge and differ by only one methyl group. This region is believed to be extremely significant for the functioning of the SCM factor, as discussed below.

C. Properties of the Isolated, Purified General Cancer-associated SCM-recognition Factor

1. Activity in the SCM Test

The purified SCM factors are fully active in the SCM test when used as a challenging agent for lymphocytes isolated from patients with several different types of malignancies. This activity can be demonstrated by assay at any point during the purification of the factor, starting at the ultrafiltrate. Details of the results of such assays are given below under "Examples."

2. Tryptic Peptides of the Factors

Purified preparations of the SCM factor from plasma of patients with lung cancer and breast cancer were subjected to tryptic digestion, followed by purification of the tryptic peptides by RP-HPLC. In each case, a particular fragment eluted at 30.4 volume percent of solvent A and 69.6 volume percent of solvent B, in RP-HPLC using the AQUAPORE™ RP-300 column. These fractions were found, by sequence analysis, to be the fragment of the SCM factor consisting of residues 8–22. (In both cases, residue 7 is lysine, and trypsin is known to cleave after lysine residues.) These tryptic peptides are fully active in the SCM test. Significantly, both tryptic fragments include the nearly invariant region of the peptide from amino acids 14–22.

3. Cross-reactivity of the SCM Factor

The isolated factor of the present invention is designated as a general cancer-associated SCM-recognition factor because lymphocytes isolated from donors with all types of cancer respond to all preparations of the factor in the SCM test.

4. Homology with $\alpha_1$-Protease Inhibitor

Computer search of the National Biomedical Research Foundation protein sequence data bank unexpectedly revealed that the amino acid sequences of the 12 isolated and purified general cancer-associated SCM-recognition factors are from 82.8% to 89.7% identical to an internal 28–33 amino acid sequence from the glycoprotein $\alpha$-1-protease inhibitor ($\alpha_1$-PI). The $\alpha_1$-PI is a glycoprotein with a molecular weight of 55,000 daltons; it is a single polypeptide chain of 394 residues, and inhibits serine proteases. The sequence of the $\alpha_1$-PI homologous to the SCM factor is, for factors from 9 out of 12 cancers, between amino acids 358 and 388 with serine at position 359 missing. For the remaining three cancers, gastric cancer, adenocarcinoma of the prostate, and seminoma of the testes, the homologous sequence is between residues 359 and 393. For the factor from seminoma testes, the homology is 100%; for the factor from prostate adenocarcinoma, the homology is 97%; and for the factor from gastric carcinoma, the homology is 94%. (These calculations exclude the unidentified residues.)

5. Synthesis of SCM Factors by Cancer Cells in Culture

Metabolically active human cancer cells grown in culture, including T10806 fibrosarcoma cells, MCF7 breast cancer cells, A2780 ovarian cancer cells, and HCT80 colon cancer cells, excreted into serum-free tissue culture media molecules that, when taken through the SCM factor purification process, exhibited optical density peaks with retention times identical to those for SCM factor itself. Partial sequencing of these peaks indicated that they are homologous with SCM factor.

These results were supported by ELISA tests using anti-SCM factor antibody (Example 14). When ELISA tests were performed on the cultured human cancer cells, the presence of SCM factor was detected in all of the cell lines tested. Different cell lines produced different quantities of SCM factor per cell under identical conditions. This variation might be an expression of differences in carcinogenic potential or metabolic activity of these different cell lines. This is supported by results showing the treatment of MCF7 breast cancer cells and T1080 fibrosarcoma cells with cycloheximide, a translational inhibitor of protein synthesis, caused a decrease in the synthesis of SCM factor. These results are in agreement with our hypothesis that cancer cells actively synthesize SCM factor molecules.

Active protein synthesis is required for production of SCM factor by cancer cells. Example 14 shows that treatment of cultured human cancer cells with the protein synthesis inhibitor cycloheximide considerably decreased the synthesis of the SCM factor as determined by the ELISA assay.

II. SYNTHETIC CANCER-ASSOCIATED SCM-RECOGNITION FACTOR

In view of the high degree of sequence homology between the SCM factors isolated from 12 different types of cancer, a synthetic SCM factor was prepared using standard solid-phase peptide synthesis methods. This synthetic SCM factor has a "consensus" sequence of 29 amino acids and shares the properties and activity of the isolated purified SCM factors.

The preparation of a synthetic SCM factor is desirable for a number of reasons: (1) availability and quantity without the necessity of isolation from cancer tissues; (2) uniformity of structure and activity; and (3) the possibility of varying the sequence in order to determine structure-activity relationships.

A. Sequence of the Synthetic SCM Factor Molecule

The synthetic SCM factor has the amino acid sequence M-I-P-P-E-V-K-F-N-K-P-F-V-F-L-M-I-D-Q-N-T-K-V-P-L-F-M-G-K (SEQ ID NO: 2).

This sequence is not the only sequence with 29 amino acids believed to possess SCM activity. It is a well-established principle of protein and peptide chemistry that certain amino acids substitutions, entitled "conservative" amino acid substitutions, can frequently be made in a protein or a peptide without altering either the confirmation or the function of the protein or peptide. Such changes include substituting any of isoleucine (I), valine (V), and leucine (L) for any other of these amino acids; aspartic acid (D) for glutamic acid (E) and vice versa; glutamine (Q) for asparagine (N) and vice versa; and serine (S) for threonine (T) and vice versa (T. E. Creighton, "Proteins: Structures and Molecular Properties" (W. H. Freeman, New York, 1984), pp. 110–112).

In view of these equivalencies, peptides of the sequence M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-L, in which: $X_2$, $X_6$, $X_{13}$, $X_{15}$, $X_{17}$, $X_{23}$, and $X_{25}$ can each be I, L, or V; $X_5$ and $X_{18}$ can each be D or E; $X_9$, $X_{19}$ and $X_{20}$ can each be Q or N; and $X_{21}$ can be S or T, are expected to have SCM factor activity. In this designation of the sequence, and corresponding designations elsewhere employing subscripts, the number appearing in the subscript indicates the position of the amino acid specified in a factor of 29 amino acids. For example, "$X_2$" refers to the second amino acid from the amino-terminus.

The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Cysteine (C) can frequently be replaced by serine when cysteine's capacity to form disulfide bonds is either undesirable or unneeded. Still other changes can be considered "conservative" in particular environments.

B. Properties of the Synthetic SCM Factor

1. Activity in the SCM Test

The synthetic SCM factor molecule is highly active in the SCM test. As little as 2 femtomoles ($2\times 10^{-15}$ moles) of the synthetic SCM factor molecule produced a significant, 20%, decrease in intracellular fluorescence polarization in the SCM test when used to challenge SCM-responding lymphocytes. This activity is specific for lymphocytes from patients with cancer.

2. Induction of SCM-recognition Receptors in Lymphocytes from Healthy Donors The synthetic SCM factor can modify the SCM response of lymphocytes from healthy donors from the response characteristic of such lymphocytes (i.e., a response to PHA and no response to a cancer-associated factor) to the response characteristic of lymphocytes from donors with cancer (i.e., no response to PHA and a response to a cancer-associated factor). This property of the synthetic SCM factor is disclosed in detail in our copending application Ser. No. 07/539,686, incorporated herein by reference.

The induction of these receptors requires protein synthesis. When the incubation is carried out in the presence of the protein synthesis inhibitors cycloheximide or actinomycin D at 10 µg/$5\times10^6$ cells, no response to synthetic SCM factor was induced, and the normal response to the mitogen PHA was not abolished.

C. Production and Activity of Fragments of Synthetic SCM Factor

In order to determine which portion or portions of the synthetic SCM factor is responsible for its activity in the SCM test, five peptide fragments of the synthetic SCM factor were synthesized, designated F1 through F5. These represented the following portions of the intact molecules: F1, amino acids 1–22; F2, amino acids 8–29; F3, amino acids 8–22; F4, amino acids 14–22; and F5, amino acids 1–13. These fragments have the following amino acid sequences:

F1:  M-I-P-P-E-V-K-F-N-K-P-F-V-F-L-M-D-Q-N-T-K (SEQ ID NO: 4);

F2: F-N-K-P-F-V-F-L-M-I-D-Q-N-T-K-V-P-L-F-M-G-K (SEQ ID NO: 5);

F3: F-N-K-P-F-V-F-L-M-I-D-Q-N-T-K (SEQ NO: 6);

F4: F-L-M-I-D-Q-N-T-K (SEQ ID NO: 3); and

F5: M-I-P-P-E-V-K-F-N-K-P-F-V (SEQ ID NO: 7).

As detailed below in Example 8, fragments F1, F2, F3, and F4 are all active in the SCM test, while fragment F5 is inactive. All of the active fragments contain the 9-amino-acid segment of F4, and it is reasonable that this segment represents the active site responsible for SCM activity.

Not only are peptides F1 through F4 active in the SCM test, variants of these peptides with conservative amino acid substitutions are also expected to have SCM activity and fall within the scope of the present invention. These conservative substitutions, as outlined above, include any of isoleucine, valine, and leucine for any other of these amino acids; aspartic acid for glutamic acid and vice versa; asparagine for glutamine and vice versa; and serine for threonine and vice versa. The existence of these conservative substitutions means that the following peptides are expected to have SCM activity:

M-$X_2$-P-P-$X_5$-$X_6$-K-F-$X_9$-K-P-F-$X_{13}$-F-$X_{15}$-M-$X_{17\text{-}X18}$-$X_{19}$-$X_{20}$-$X_{21}$ -K;

F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-K;

F-$X_9$-K-P-F-$X_{13}$-F-$X_{15}$-M-$X_{17}$-$X_{18}$-$X_{19}$-$X_{20}$-$X_{21}$-K; and

F-$X_{15}$-M-$X_{17}$-$X_{18}$-$X_{19}$-$X_{20}$-$X_{21}$-K.

In these sequences, the subscripts designating particular amino acid residues have the same meaning as stated above in the discussion of conservative amino acid substitutions in the entire 29-amino-acid synthetic SCM factor.

III. USE OF THE PURIFIED AND SYNTHETIC SCM FACTORS

Both the purified and synthetic SCM factors can be used as challenging agents in the SCM test, can be used to prepare antisera for the detection of the SCM factor, and can be used for the generation of DNA sequences that carry equivalent genetic information for use in a variety of genetic engineering procedures. As discussed below, this SCM factor can also be used in the management of cancer.

A. Performance of the SCM Test

The activity of both the purified SCM factor and the synthetic SCM factor, as well as the fragments of the SCM factor, is confirmed by its effect on viable SCM-responding lymphocytes in accordance with the prior publication by L. Cercek and B. Cercek, "Application of the Phenomenon of Changes in the Structuredness of Cytoplasmic Matrix (SCM) in the Diagnosis of Malignant Disorders: A Review," *Europ. J. Cancer* 13, 903–915 (1977). The general cancer-associated SCM-recognition factor of the present invention produces a significant decrease in the intracellular fluorescence polarization value of potentially SCM-responding lymphocytes from donors afflicted with cancer when used to challenge such lymphocytes in the SCM test as performed as described in that article. The degree of decrease of the intracellular fluorescein fluorescence polarization value of such challenged lymphocytes is substantial—at least 20% even if ultrafiltrate from plasma from donors afflicted with cancer is used to challenge such lymphocytes, and as great as 40–55% if purified RP-HPLC fractions or synthetic peptides are used.

Two previously established procedures are important for the proper performance of the SCM test as reported herein. These procedures are the isolation of potentially SCM-responding lymphocytes and the technique of measuring the fluorescence polarization values themselves, and their conversion into numbers meaningful for the SCM test. These procedures are detailed in previous U.S. patent application Ser. No. 07/539,686 by Drs. Boris and Lea Cercek, previously incorporated by reference. Therefore, these procedures need not be set forth in detail herein.

The result of the SCM test is a value for the intracellular fluorescein fluorescence polarization of the challenged lymphocytes. This value is designated as a P value. The higher the measured P value, the greater the degree of polarization. The term "$P_S$" is used to refer to the P value of an aliquot of lymphocytes that has been challenged with a challenging agent such as an SCM factor of the present invention. Similarly, the term "$P_C$" is used to refer to the P value of an aliquot of lymphocytes not challenged with a challenging agent. When $P_S$ is compared with $P_C$, a ratio of $P_S$ to $P_C$ of less than about 0.9 is an indication of the presence of malignancy in the body of the donor of the challenged lymphocytes.

A preferred method of using the SCM factor as a challenging agent in the SCM test comprises comparing $P_S$ to the fluorescence polarization value, $P_M$ of another aliquot of the lymphocytes contacted with a mitogen such as phytohaemagglutinin (PHA), to determine an SCM response ratio, $RR_{SCM}$, where $RR_{SCM} = P_S \div P_M$. An $R_{SCM}$ of less than about 0.9 indicates the presence of a malignancy. The use of the $RR_{SCM}$ is preferable because lymphocytes from donors free of malignancy respond to PHA but not to cancer-associated SCM factors, while lymphocytes from donors with malignancy do not respond to PHA but do respond to cancer-associated SCM factors. This double change in response pattern gives a sharper indication of the presence of a malignancy.

B. Detection of SCM-specific Receptors

It is believed that the effects of SCM factor on SCM-responding lymphocytes are mediated by the specific binding of SCM factor to SCM-factor-specific receptors located in the cell membrane of the lymphocytes. These receptors can be detected by the use of labeled SCM molecules, such as radiolabeled SCM factor, fluorescence-labeled SCM factor, enzyme-labeled SCM factor, or SCM factor labeled with a chemiluminescent label. Alternatively, SCM factor can be conjugated to biotin. Avidin or streptavidin can then be labeled with enzymes, fluorescent labels, or radioactive labels. The labeled avidin or streptavidin can be used to bind the biotin-conjugated SCM factor for labeling.

C. Use of the SCM Factor in the Detection of Cancer

As previously detailed in our patent application Ser. No. 07/539,686, the SCM factor of the present invention can be used for a number of purposes in the detection of cancer.

1. Use of SCM Factor as Challenging Agent

SCM factor, or any of its active fragments, can be used as a challenging agent in the SCM test for the detection of cancer. Lymphocytes from donors with cancer, but not from donors free of cancer, are primed to respond to cancer-associated factors in the SCM test. Accordingly, only lymphocytes from donors with cancer respond to SCM factor with a decrease in intracellular fluorescein fluorescence polarization value in the SCM test. This response constitutes an early warning that cancer cells producing SCM factor are present in the body of the lymphocyte donor, even when the number of tumor cells or the size of the tumor might not be otherwise detectable.

2. Detection of Receptors Specific for SCM Factor

SCM factor molecules or fragments that are labeled can be used to detect the presence of receptors for SCM molecules on the SCM-responding fraction of lymphocytes. The label can be, but is not limited to, a radioactive label, a fluorescent label, a chemiluminescent label, or an enzyme label. The presence of these receptors is itself an indication of cancer. They can be detected using flow cytometry, fluorescence microscopy, enzyme-linked assays, or other assays for lymphocyte receptors. If the SCM molecules are labeled with radioactive isotopes, autoradiography, scintigraphy, and other detection methods for radionuclides can be used to detect the presence of receptors for SCM factors.

If SCM-responding lymphocytes are isolated, washed, and incubated with a saturating quantity of labeled SCM factor, the extent of the binding of the SCM factor to the lymphocytes indicates the number of SCM factor receptors present per lymphocyte. This test can be used to indicate the sensitization of SCM-responding lymphocytes to the SCM factor and can be used as an alternative to the SCM test to detect the presence of cancer; it can also be used to confirm the findings of the SCM test.

3. Detection of SCM Factor Molecules in Cancer Biopsies

By flow cytometry, fluorescence microscopy, or enzyme-linked assays, SCM factor molecules can be detected in cancer biopsies using appropriately labeled anti-SCM factor antibodies. Because SCM factor molecules are produced in quantity by cancer cells, their presence in biopsy specimens is a strong confirmation of the cancerous nature of the tissues from which the biopsy specimen is taken. The detection of SCM factor molecules in cancer biopsies by immunochemical assays is discussed in detail below in Part IV, "Immunochemistry of the Natural and Synthetic SCM Factors."

4. Detection of SCM Factor Molecules in Body Fluids

As shown above, SCM factor molecules are excreted by cancer cells into body fluids such as blood plasma or urine. The presence of SCM factor in body fluids can therefore be used as a general cancer-specific marker. The detection of SCM factor molecules in body fluids by immunochemical assays is also discussed in detail below in Part IV.

IV. IMMUNOCHEMISTRY OF THE NATURAL AND SYNTHETIC SCM FACTORS

A. Preparation of Antibodies

Antibodies can be prepared to both the natural and synthetic SCM factors described above, as well as fragments thereof.

1. General Methods for Antibody Preparation

Methods for antibody preparation are well known in the art. Such methods are described, for example, in E. Harlow and D. Lane, "Antibodies: A Laboratory Manual," Cold Spring Harbor Laboratory, 1988, incorporated herein by this reference. Intact SCM factors of 29–35 amino acid residues, both natural and synthetic, are sufficiently large to be immunogenic when injected into antibody-forming animals. Preferably, injection is with Freund's adjuvant, most preferably with complete Freund's adjuvant.

For the smaller fragments of SCM factor peptides, a preferred method of antibody production comprises conjugating the peptide to a carrier protein and using the resulting conjugate as an immunogen. Preferably the immunogen is administered with Freund's adjuvant. Fragments of SCM factor to which antibodies can be prepared in this matter include the following:

(i) F-L-M-I-D-Q-N-T-K (SEQ ID NO: 3);
(ii) F-N-K-P-F-V-F-L-M-I-D-Q-N-T-K (SEQ ID No: 6);
(iii) F-N-K-P-F-V-F-L-M-I-D-Q-N-T-K-V-P-L-F-M-G-K (SEQ ID NO: 5); and
(iv) M-I-P-P-E-V-K-F-N-K-P-F-L-M-I-D-Q-N-T-K (SEQ ID NO: 4), as well as derivatives thereof incorporating one or more conservative amino acid substitutions.

Suitable carrier proteins and conjugation methods are well-known in the art. Suitable carrier proteins include, but are not limited to keyhole limpet hemocyanin, bovine serum albumin, ovalbumin, polylysine, and purified protein derivative of tuberculin (PPD).

A large number of coupling agents are well-known in the art, including, but not limited to bis(sulfosuccinimidyl) suberate, dimethyl adipimate, dimethyl pimelimidate, dimethyl suberimidate, disuccinimidyl suberate, glutaraldehyde, m-maleimidobenzyl-N-hydroxysuccinimide, sulfo-m-maleimidobenzyl-N-hydroxysuccinimide, sulfosuccinimidyl 4-(N-maleimidomethyl)-cyclohexane-1-carboxylate, sulfosuccinimidyl 4-(p-maleimidophenyl) butyrate, and N-succinimidyl bromoacetate. For heterobifunctional crosslinkers in which one of the functionalities reacts with a sulfhydryl group, such as N-succinimidyl bromoacetate, the peptide to be coupled can be extended at its carboxyl terminus by an additional cysteine residue for coupling (N. S Bernatowicz and G. R. Matsueda, "Preparation of Peptide-Protein Immunogens Using N-Succinimidyl Bromoacetate as a Heterobifunctional Cross-Linking Agent," *Anal Biochem.* 155:95–102 (1986)).

The intact 29–35 amino acid natural and synthetic SCM factors described above can also be coupled to a carrier protein for antibody production, optionally after addition of a cysteine residue at their carboxy terminus.

Monoclonal antibodies can be prepared according to methods well known in the art (Harlow and Lane, supra). These methods result in the generation of immortal hybridoma cells producing monoclonal antibodies of the desired specificity.

2. Specific Antibodies

Particularly useful are two antibodies: (1) antibodies produced by immunization of an antibody-producing animal with the peptide M-I-P-P-E-V-K-F-N-K-P-F-V-F-L-M-I-D-Q-N-T-K-V-P-L-F-M-G-K-C (SEQ ID NO: 1) conjugated at its carboxy-terminal cysteine residue to a carrier protein; and (2) antibodies produced by immunization of an antibody-producing animal with the peptide M-I-P-P-E-V-K-F-N-K-P-F-V-F-L-M-I-D-Q-N-T-K-V-P-L-F-M-G-K (SEQ ID NO: 2).

These antibodies can be polyclonal or monoclonal. The monoclonal antibodies can be mouse, rat, human, or hybrid depending on the animal immunized and the myeloma used as fusion partner, as disclosed in J. W. Goding, "Monoclonal Antibodies: Principles and Practice," 2d ed., Academic Press, London, 1986, incorporated herein by this reference.

Also within the scope of the invention are monovalent or divalent antibody fragments produced from the above-described antibodies, such as Fab, Fab' or F(ab')$_2$. Additionally, within the scope of the invention are antibodies of hybrid specificity produced by in vitro reassociation of antibody subunits.

B. Specificity Of Antibodies Prepared to SCM Factor Molecules and Fragments

Among antibodies according to the present invention are antibodies that are capable of binding cancer recognition factors (SCM factor molecules) and fragments of SCM factor molecules. These antibodies are prepared as described above, by immunization of an antibody-producing with an appropriate SCM factor or fragment. For fragments, the fragment is typically conjugated to a carrier protein as described above. The antibodies can be polyclonal or monoclonal.

Although not wishing to be bound to any particular theory, it is not necessary to immunize with each peptide or fragment discussed below to produce antibodies capable of binding specifically to that peptide or fragment. Typically, epitopes for protein or peptide antigens are about 9–15 amino acids long (I. Wilson et al., "The Structure of an Antigenic Determinant," Cell 37:767–778 (1984)), so changes outside the region of the antigenic determinant may not affect the binding of the antibody. Thus, antibodies that are prepared by immunization with one SCM factor or fragment may bind to another if the differences in the sequence between the peptide used for immunization and the peptide bound are outside the antigenic determinant. This binding may be sufficiently specific to allow one antibody to recognize more than one peptide or fragment, and is not a cross-reaction.

Although not wishing to be bound by any particular theory, the region for amino acid residues 14–22 of the SCM factor is invariant except for the highly conservative substitution of E for D in some preparations. This domain is of the correct size to constitute an epitope, and it is highly plausible that this highly conserved region constitutes the epitope against which antibodies are made and for which they are specific. That is supported by the fact of the addition of a carboxy-terminal C to the peptide for conjugation to a carrier protein does not alter the specificity of the resulting antibody.

In the event that the specificity of the antibodies depends on the core sequence, it is believed that changes in the factor outside the core sequence do not alter the specificity of the resulting antibodies.

Antibodies of the present invention include an antibody that specifically binds a peptide selected from the group consisting of M-I-P-P-E-V-K-F-K-N-P-F-V-F-L-M-I-D-Q-N-T-K-V-P-L-F-M-G-K (SEQ ID NO: 2) and a peptide related thereto by one or more conservative amino acid substitutions.

Antibodies of the present invention further include an antibody specifically binding a cancer recognition factor, the factor being a peptide of at least nine amino acid residues including a core sequence of nine amino acid residues. The core sequence is F-$X_{15}$-M-$X_{17}$-$X_{18}$-$X_{19}$-$X_{20}$-$X_{21}$-K. In this sequence, $X_{15}$ and $X_{17}$ are each independently selected from the group consisting of I, L, and V. $X_{18}$ is selected from the group consisting of D and E. $X_{19}$ and $X_{20}$ are each independently selected from the group consisting of Q and N. $X_{21}$ is selected from the group consisting of S and T. The factor is capable of producing at least a 10% decrease in the intracellular fluorescence polarization value of lymphocytes capable of responding in the SCM test from donors afflicted with cancer.

Preferably, the core sequence is F-L-M-I-D-Q-N-P-K (SEQ ID NO: 3).

In one alternative, the cancer-recognition peptide for specifically binding the antibody can have 9 amino acid residues and can have the sequence F-$X_{15}$-M$X_{17}$-X $_{18}$-$X_{19}$-$X_{20}$-$X_{21}$-K. Preferably, in this alternative, the peptide has the sequence F-L-M-I-D-Q-N-T-K (SEQ ID NO: 3).

In another alternative, the cancer-recognition peptides specifically bound by the antibody can have 15 amino acid residues and have the sequence $F_9$-K-P-F-$X_{13}$-F-X $_{15}$-M-$X_{17}$-$X_{18}$-$X_{19}$-$X_{20}$-$X_{21}$-K. In this alternative, $X_9$ is independently selected from the group consisting of Q and N and $X_{13}$ is independently selected from the group consisting of L and V. $X_{15}$, $X_{17}$, $X_{18}$, $X_{19}$, $X_{20}$, and $X_{21}$ are as defined above. Preferably, the cancer-recognition peptide has the sequence F-N-K-P-F-V-F-L-M-I-D-Q-N-T-K (SEQ ID NO: 6).

In yet another alternative, the cancer-recognition peptides specifically bound by the antibody can have 22 amino acid residues and can have the sequence M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-$X_{21}$-K. In this alternative, $X_2$ and $X_6$ are each independently selected from the group consisting of I, L, and V. $X_5$ is independently selected from the group consisting of D and E. $X_9$ is independently selected from the group consisting of Q and N. $X_{13}$, $X_{15}$, $X_{17}$, $X_{18}$, $X_{19}$, $X_{20}$, and $X_{21}$ are as defined above. Preferably, the cancer-recognition peptide has the sequence M-I-P-P-E-V-K-F-N-K-P-F-V-F-L-M-I-D-Q-N-K-T-K (SEQ ID NO: 4).

In yet another alternative, the cancer-recognition peptide specifically bound by the antibody can have 22 amino acid residues and can have the sequence F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-K. In this sequence, $X_{23}$ and $X_{25}$ are each independently selected from the group consisting of I, L, and V. $X_9$, $X_{11}$, $X_{13}$, $X_{15}$, $X_{17}$, $X_{18}$, $X_{19}$, $X_{20}$, and $X_{21}$ are as defined above. Preferably, the cancer-recognition peptide has the sequence F-N-K-P-F-V-F-L-M-I -D-Q-N-T-K-V-P-L-F-M-G-K (SEQ ID NO: 5) .

Antibodies according to the present invention further include an antibody specifically binding a cancer-recognition factor having an amino acid sequence of M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-X $_{21}$-K-$X_{23}$-P-$X_{25}$-F-M-G-P. In this sequence, $X_2$, $X_6$, $X_9$, $X_{13}$, $X_{15}$, $X_{17}$, $X_{18}$, $X_{19}$, $X_{20}$, $X_{21}$, $X_{23}$, and $X_{25}$ are as defined above with regard to the smaller peptides.

Preferably, the factor has the sequence M-I-P-P-E-V-K-F-N-K-P-F-V-F-L-M-I-D-Q-N-T-K-V-P-L-F-M-G-K (SEQ ID NO: 2).

Antibodies of the present invention further include antibodies specifically binding a cancer-recognition factor of from 29–35 amino acids in length and including a core sequence at amino acids 14–22. The core sequence is F-L-M-I-D-$X_{18}$-Q-N-T-K, wherein $X_{18}$ is selected from the group consisting of D and E.

The antibodies capable of binding the above-described cancer-recognition factor include antibodies specifically binding the following cancer-recognition factors:

(1) A cancer-recognition factor of the sequence V-I-P-P-E-V-K-F-N-K-P-F-V-F-L-M-I-D-Q-N-T-K-V-P-L-F-M-G-K (SEQ ID NO: 8).

(2) A cancer-recognition factor of the sequence M-I-P-P-E-V-K-F-N-K-P-F-V-F-L-M-I-D-Q-N-T-K-C-P-C-F-M-G-C (SEQ ID NO: 9).

(3) A cancer-recognition factor of the sequence $X_1$-I-P-P-E-V-K-F-N-K-P-F-V-F-L-M-I-D-Q-N-T-K-C-C-L-F-M-G-K, wherein $X_1$ is selected from the group consisting of M and V.

(4) A cancer-recognition factor of the sequence $X_1$-I-P-P-E-V-K-F-N-K-P-F-V-F-L-M-I-D-Q-N-T-K-R-P-F-M-G, wherein $X_1$ is selected from the group consisting of R and S.

(5) A cancer-recognition factor of the sequence V-I-P-P-E-V-K-F-N-K-P-F-V-F-L-M-I-D-Q-N-T-K-C-P-L-F-M-G-K (SEQ ID NO: 10).

(6) A cancer-recognition factor of the sequence V-I-P-P-E-V-K-F-N-C-P-F-V-F-L-M-I-D-Q-N-T-K-V-P-L-F-M-G-K (SEQ ID NO: 11).

(7) A cancer-recognition factor selected from the group consisting of peptides having amino acid sequences $X_1$-I-P-P-E-V-K-F-N-K-P-F-V-F-L-M-I-D-Q-N-T-K-C-P-C-F-M-G-C and $X_1$-I-P-P-E-V-K-F-N-K-P-F-V-F-L-M-I-D-Q-N-T-K-C-P-C-F-M-G-C-V-V-N-C-T-E, wherein $X_1$ is selected from the group consisting from R and S.

(8) A cancer-recognition factor selected from the group consisting of peptides having amino acid sequences X$_1$-I-P-P-E-V-K-F-N-K-P-F-V-F-L-M-I-E-Q-N-T-K-S-P-L-F-L-G-K and X$_1$-I-P-P-E-V-K-F-N-K-P-F-V-F-L-M-I-E-Q-N-T-K-S-P-L-F-M-G-K-V-V-N-P-T-Q, wherein X$_1$ is selected from the group consisting of V and S.

(9) A cancer-recognition factor of the sequence X$_1$-I-P-P-E-V-K-F-N-K-P-F-V-F-L-M-I-E-Q-N-T-K-S-P-L-F-M-G-K-V-V-N-P-T-Q, wherein X$_1$ is selected from the group consisting of S and V.

C. Immunoassays to SCM Factor

Once antibodies to SCM factor are produced, either polyclonal or monoclonal, they are used in any type of immunoassays, including, but not limited to: competitive or non-competitive sandwich immunoassay; colorimetric assays (e.g., ELISA, PGLIA (prosthetic-group-label immunoassay), SLIFIA (substrate-labeled fluorescence immunoassay), etc.); radiometric procedures such as radioimmunoassay (RIA); and assays employing luminescence, including bioluminescence and direct or catalyzed chemiluminescence). The direct chemiluminescence procedures can use luminophores such as acridinium derivatives; the catalyzed chemiluminescence procedures can use either enzymatic, such as horseradish peroxidase, or non-enzymatic catalysts such as metals.

A large number of immunoassays are known in the art and are summarized in M. Oellerich, "Enzyme-Immunoassay: A Review," *J. Clin. Chem. Clin. Biochem,* 22:895–904 (1984) and C. Blake and B. J. Gould, "Use of Enzymes in Immunoassay Techniques," *Analysis* 109:533–547 (1984), both of which are incorporated herein by this reference. For all of these types of immunoassays except for immunoassays dependent on aggregation of antigen-antibody complexes (i.e., formation of a lattice), monovalent fragments of antibodies, such as Fab or Fab' fragments, can substitute in some applications for intact bivalent antibody molecules.

The label used for detection in the immunoassay depends on the sensitivity required and the details of the particular immunoassay. Suitable labels include fluorescent labels, enzyme labels, chemiluminescent labels, bioluminescent labels, radioactive labels, metal sol labels, latex labels, and colorimetric labels.

One particularly useful type of immunoassay is the enzyme-linked immunosorbent assay (ELISA assay). A competitive ELISA assay for detection of SCM factor is discussed below in Example 10. Briefly, this competitive ELISA assay entails:

(1) attachment of SCM factor or an immunologically equivalent analog thereof to a solid phase capable of binding protein;

(2) addition of the sample to be assayed;

(3) incubation of the solid phase with a first antibody specific to SCM factor;

(4) incubation with a second antibody that is specific for the first antibody, the second antibody being labeled with an enzyme producing a colorimetrically detectable product when incubated with a substrate;

(5) addition of a substrate for the enzyme; and (6) measurement of the absorbance of the detectable product.

Because this assay is a competitive assay, only the enzyme bound to antibody attached to the solid phase yields color. The presence of SCM factor in the test sample competitively inhibits the binding of the antibody to the SCM factor on the solid phase and thus reduces the yield of color.

Preferably, the solid phase to which the SCM factor or immunological analogue is attached is plastic. The attachment of peptides and proteins to plastic is well known in the art and is described, for example, in P Tijssen, "Practice and Theory of Enzyme Immunoassays" (Elsevier, Amsterdam, 1985), pp. 297–314, incorporated herein by this reference. Preferably, the first antibody is rabbit-SCM factor antibody, the second antibody is goat anti-rabbit IgG antibody labelled with alkaline phosphatase, and the substrate is p-nitrophenyl phosphate.

Preferably, the measurement of the absorbance is performed at the wavelength of the maximum absorbance of the detectable product, i.e., 405 mm for p-nitrophenyl. However, in some cases, it can be desirable to perform the measurement at a wavelength different from the wavelength of maximum absorbance of the product to minimize interference from another compound present in the assay.

The ELISA test is typically performed at room temperature, although it can be performed at 4° C. or 37° C., as well as any temperature in between. The time of incubation of the solid phase with the first antibody is typically from about 2 minutes to about 1 hour, more typically from about 10 minutes to about 30 minutes. The incubation with the second antibody is typically from about 5 minutes to about 1 hour, more typically about 10 minutes to 30 minutes. The assay can be performed in any suitable buffer such as phosphate buffered saline (PBS) or in Tris-HCl. Typically, the assay is performed at a pH of about 6 to about 8; preferably, the pH is about 7.2 to about 7.8. In some cases, it may be desirable to add non-immune immunoglobulin such as goat serum to prevent non-specific cross-reactions caused by aggregation of small quantities of protein. The ELISA can be used to detect the level of SCM factor in ultrafiltrates of blood plasma (Example 12), the presence of SCM factor in purified preparations from serum-free supernatant cancer cell media (Example 13) and the presence of SCM factor in cultured human cancer cells (Example 14).

Alternatively, for samples having relatively low protein content, a non-competitive ELISA can be performed by allowing peptides and proteins in the sample, including any SCM factor present, to bind to the solid support and then reacting with the anti-SCM antibody discussed above. The second enzyme-labeled antibody specific to the first antibody is then added as discussed above. Substrate for the enzyme is then added, and, after an appropriate incubation, the absorbance of the product is measured. For this version of the ELISA, the higher the measured absorbance, the greater the quantity of SCM factor originally present in the sample.

Because of potential cross-reactivity of SCM-factor antibodies with $\alpha_1$-PI because of the sequence homology between them, it is preferable to perform the ELISA in a manner in which any possible immunochemical interference from $\alpha_1$-PI or any other partially homologous peptide sequence is eliminated or corrected for. Preferably, a two-analyte immunoassay is performed as discussed below in Section D.

Alternatively, the $\alpha_1$-PI molecules can be removed from the sample by one of a number of techniques, including, but not limited to, ultrafiltration through a filter with a nominal molecular weight cutoff of from 1,000–3,000 daltons or any other molecular weight cutoff that efficiently eliminates $\alpha_1$-PI, which has a molecular weight of about 52,000, by passage through chromatography columns, or by binding of $\alpha_1$-PI to immobilized proteases such as trypsin, with which $\alpha_1$-PI forms a stable complex.

D. The Two-Analyte Immunoassay for Detection of SCM Factor in the Presence of a Partially Homologous Inflammation-Related Protein As discussed in Section C, above, it is preferred to perform the immunoassay for the SCM factor as a two-analyte assay so that interference from partially homologous peptide sequences is corrected for. A particular example of such a partially homologous peptide sequence is $\alpha_1$-PI or fragments thereof. Such an assay typically is performed on cells, cell supernatants, or cell fractions to detect the presence of SCM factor therein. This assay is performed as follows:

(1) incubating a first aliquot of the sample with a first antibody specific for the cancer-recognition factor to bind the first antibody to the cancer-recognition factor and to the partially homologous peptide sequence in the first aliquot;

(2) incubating a second aliquot of the sample with a second antibody specific for a portion of the partially homologous peptide sequence lacking any substantial homology with any portion of the sequence of the cancer-recognition factor to bind the second antibody only to the partially homologous peptide sequence in the second aliquot; and (3) comparing the quantity of the first antibody bound to the first aliquot with the quantity of the second antibody bound to the second aliquot to detect the cancer recognition factor.

This assay takes advantage of the fact that the amino-terminal region of the $\alpha_1$-PI molecule (also known as $\alpha_1$-antitrypsin) lacks any substantial homology with any portion of the sequence of the cancer-recognition factor. As disclosed previously in application Ser. No. 07/539,686, incorporated herein by reference, the SCM-active cancer-recognition factor disclosed therein is homologous to a region of $\alpha_1$-PI extending from residues 358 to 388 or 393 of $\alpha_1$-PI, i.e., near the carboxy terminus of $\alpha_1$-PI. Therefore, an antibody specific for the amino-terminal region of $\alpha_1$-PI binds only to $\alpha_1$-PI and does not bind to SCM-active cancer recognition peptides, while an antibody specific for the SCM-active cancer-recognition peptides does bind to the corresponding portion of the $\alpha_1$-PI molecule. Accordingly, the use of antibodies specific for the non-homologous portion of a partially homologous peptide sequence in conjunction with antibodies specific for the SCM-factor peptide or a portion thereof provides an improved way of detecting an SCM-active cancer recognition factor in the presence of a partially homologous peptide sequence.

Preferably, the sample subjected to this assay is a cellular sample, such as a sample believed to contain cancer cells. Alternatively, the sample can be a sample of body fluid, particularly urine or saliva.

The quantity of the first antibody bound to the first aliquot can be compared with the quantity of the second antibody bound to the second aliquot by obtaining a ratio between the two quantities. A ratio of less than 1 is indicative of the presence of SCM factor. A ratio of greater than 1 indicates that SCM factor is not present.

Typically, the partially homologous peptide sequence comprises at least a segment of an inflammation-related protein, such as $\alpha^1$-PI. Preferably, the first antibody, specific for a segment of a partially homologous peptide sequence lacking any substantial homology with the sequence of the SCM-factor peptide, is specific for the amino-terminal portion of $\alpha_1$-PI. More preferably, the amino-terminal portion of $\alpha_1$-PI is the amino-terminal 19 amino acids. The second antibody, to the SCM factor, can be any of the anti-SCM antibodies discussed above. However, several antibodies are preferred for use in this assay because of their binding to SCM-factor peptides or highly conserved fragments thereof:

(1) an antibody that specifically binds a peptide selected from the group consisting of M-I-P-P-E-V-K-F-N-P-F-V-F-L-M-I-D-Q-N-T-K-V-P-L-F-M-G-K ((SEQ ID NO: 1) and a peptide related thereto by one or more conservative amino acid substitutions;

(2) an antibody specifically binding the peptide M-I-P-P-E-V-K-F-N-K-P-F-V-F-L-M-I-D-Q-N-T-K-V-P-L-F-M-G-K (SEQ ID NO: 2); and (3) an antibody specifically binding the peptide F-L-M-I-D-Q-N-T-K (SEQ ID NO: 3).

Typically, the separate aliquots of the assay are reacted in the non-competitive ELISA assay as discussed above with the appropriate antibodies. The step of comparing the quantity of the first antibody bound to the first aliquot with the quantity of the second antibody bound to the second aliquot can comprise:

(1) reacting the incubated aliquots separately with a detection antibody specific for the first and second antibodies, the detection antibody being coupled to a detectable label; and (2) detecting the label.

Typically, the first and second antibodies are both rabbit IgG antibodies and the detection antibody specific for both the first and second antibodies is an antibody specific for rabbit IgG. However, it is to be understood that other non-human mammalian IgG antibodies can be utilized as the first and second antibody, as long as the first and second antibody come from the same species. Such antibodies, for example, could be goat, sheep, or horse antibodies.

The label can be selected from the group consisting of an enzyme label, a fluorescent label, a radioactive label, a colorimetric label, a metal sol label, and a chemiluminescent label. Preferably, the label is an enzyme label such as β-galactosidase, horseradish, glucose oxidase, or alkaline phosphatase. Most preferably, the enzyme label is alkaline phosphatase.

Many substrates for alkaline phosphatase are known in the art. A preferable substrate is p-nitrophenyl phosphate.

Alternatively, the first and second antibodies can each be coupled to a member of, e.g., the avidin-biotin specific binding pair. Both the first and second antibodies are coupled to the same member of the binding pair, i.e., either to avidin or to biotin. In this alternative, the step of comparing the quantity of the first antibody bound to the first aliquot to the quantity of the second antibody bound to the second aliquot comprises:

(1) reacting the incubated first and second aliquot separately with a detectable label, the detectable label being coupled to the specific binding pair member complementary to the specific binding pair member that is coupled to the first and second antibody; and (2) separately detecting the label bound to the first and second aliquots in order to determine the presence of the SCM factor.

The two-analyte assay can detect SCM factors in the nanogram range.

EXAMPLES

The following Examples illustrate: (1) the isolation, purification, characterization, and activities of substantially purified SCM factor from body fluids of patients with cancer; (2) the characterization and activities of synthetic SCM factor and peptides comprising partial sequences of synthetic SCM factor; and (3) the preparation and use of antibodies specific for SCM factors. These Examples are for illustrative purposes only and are not to be construed as limiting the invention.

EXAMPLE 1

Initial Purification of the General Cancer-Associated SCM Factor from Blood Plasma Blood samples from patients positively diagnosed as having active cancer, such as cancer of the breast, lung, colon, ovary, cervix, uterus, larynx, or skin (basal cell carcinoma and malignant melanoma) were collected into heparinized vials such as VACUTAINER™ tubes. Twenty-milliliter portions of the blood samples were centrifuged at about 1200 x g for approximately 40 min. The plasma above the sedimented blood cells was collected and filtered by pressure through a porous membrane filter such as an AMICON™ UM2 or YM2 filter, with a 1000-dalton molecular weight cutoff. These ultrafiltrates were lyophilized or stored at 4° C. until further purification. When these ultrafiltrates were used in the SCM test procedure described above, in every case, the ultrafiltrates caused the SCM-responding lymphocytes to respond characteristically with a decrease in P value, as they would have if they had been contacted with the cancerous tissue itself or with extracts of cancerous tissue.

EXAMPLE 2

Further Purification of the SCM Factor of Example 1

The lyophilized powder from the samples of Example 1 was dissolved in 2 ml of sterile preservative-free water for injections. At this stage, the SCM activity of the preparations was ascertained, and active samples from donors with the same type and site of cancer were pooled. The pooled samples were desalted on an 0.9×18 cm column of SEPHADEX™ G-10, which has a fractionation range of from 0 to 700 daltons. The sample volume per column chromatographic run did not exceed 25% of the column volume. Elution was carried out with double distilled water at the linear elution speed of 8 to 9 cm/hr. The desalting was carried out at room temperature (21°–23° C.). One-ml fractions eluting at between 0.3 and 0.5 times the total chromatographic bed volume were collected and the optical densities of the fractions determined. The SCM activity was contained within the first elution peak. The presence of SCM activity in that peak was confirmed by an SCM test. An aliquot of the first elution peak, prepared from an ultrafiltrate originally derived from plasma of a patient with breast cancer reduced the P value of lymphocytes from a patient with breast cancer to 86.3% of the control value in the SCM test, indicating the presence of SCM activity. These fractions were collected and lyophilized.

The eluate was further purified by fractionation on a SEPHADEX™ G-50 gel filtration column, which has a fractionation range of from 1500 to 30,000 daltons. The lyophilized desalted samples were dissolved in 50 mM $NH_4HCO_3$, loaded at no more than 5% of the column volume on a 0.9×18 cm SEPHADEX™ G-50 column at the linear elution speed of 3 cm/hr. The elution was carried out at room temperature, and one-milliliter fractions eluting from the column at between 0.4 and 0.6 times the total chromatographic bed volume were collected. These fractions were tested for SCM activity. The SCM-active fractions were contained within the first elution peak as determined by optical densities of the one-milliliter fractions after testing of the fractions in the SCM test.

Once the fractions were tested for SCM activity, the active fractions from the same cancer types were pooled and lyophilized.

For further purification the lyophilized samples were dissolved in 10 mM $NH_4HCO_3$ and loaded at no more than 4% of the column volume on an 0.8×26 cm column of Whatman DE-52 microgranular DEAE-cellulose. The column was washed with 10 ml of 10 mM aqueous $NH_4HCO_3$ increasing by 0.108% per minute from 10 mM to 1M $NH_4HCO_3$. One-milliliter fractions were collected and the optical absorption at 220 nm was determined for each fraction. Based on the optical absorbance, active fractions eluting from the column at between 4.5 and 4.7 times the total chromatographic bed volume were pooled and lyophilized for testing and further purification. These fractions showed SCM activity when tested in the SCM test as described above. The SCM activity was specific for cancer, as lymphocytes from patients free of cancer did not respond to these fractions in the SCM test.

EXAMPLE 3

Final Purification of SCM Factor of Example 2 by RP-HPLC

The DE-52 general cancer-associated SCM-active fractions of Example 2 were then reconstituted and purified to homogeneity by reverse phase high pressure liquid chromatography (RP-HPLC) using a 2.1 mm×22 cm HPLC column. The column was packed with AQUAPORE RP-300™ (7 microns). The mobile phases used in the RP-HPLC purification step were as follows:

Phase A: 0.1 volume percent aqueous trifluoroacetic acid (TFA).

Phase B: 0.09 volume percent aqueous TFA in aqueous 70% acetonitrile.

Lyophilized DE-52 SCM-active fractions were reconstituted with sterile water for injections (without preservatives) and 250 microliter aliquots were injected into the RP-HPLC column. The mobile phase flow rate was 50 microliters per minute and its composition profile was 10 minutes of 90 volume percent of Phase A, 10 volume percent of Phase B, followed by 30 minutes of linear increase of Phase B at the rate of 3 volume percent per minute. The optical density peaks detected by optical absorbance at 220 nm were hand-collected via a "nanobore" teflon tubing into 1.5 ml plastic conical Eppendorf centrifuge tubes and the solvent was evaporated in a vacuum centrifuge. In all cases, the general cancer-associated SCM-recognition factor eluted from the column at 74 volume percent of Phase B. The eluted SCM factor had activity in the SCM test. The activity was specific for cancer, as lymphocytes from patients free of cancer did not respond in the SCM test to the eluted factor.

EXAMPLE 4

Alternative RP-HPLC Purification of SCM Factor

Alternatively, the SCM factor can be purified by performing HPLC using a 4.6 mm×25 cm HPLC column packed with Ultrasphere ODS™ (5 microns) distributed by Beckman Instruments, Inc. with the DEAE-52 SCM-active fractions of Example 2. The mobile phases used with this column were as follows:

Phase A: 0.1 volume percent aqueous trifluoroacetic acid (TFA).

Phase B: 0.1 volume percent TFA in aqueous 70% acetonitrile.

The same general procedure was followed with this column as for the AQUAPORE™ column, except that the mobile phase flow rate was 1.00 ml per minute and its composition profile was 5 minutes of 70 volume percent of Phase A, 30 volume percent of Phase B, followed by 20 minutes of linear increase of Phase B at the rate of 3.5 volume percent per minute. The optical density peaks were detected at 220 nm and were hand-collected into siliconized glass test tubes and the solvent was evaporated in a vacuum centrifuge. When this HPLC system was used, in all cases the purification of general cancer-associated SCM-recognition factor from nineteen different cancer types, including squamous cell carcinoma of the cervix, adenocarcinoma of the breast, adenocarcinoma of the bronchus, and malignant melanoma, always yielded a single optical density peak of activity, eluting at 56.3 volume percent of Phase B. This activity was specific for cancer.

EXAMPLE 5

Identification and Isolation of SCM-Active Tryptic Peptides from SCM Factor Purified from Blood Plasma of Patients with Breast Cancer and Lung Cancer le;2qTryptic peptides with SCM activity were isolated from the purified SCM factors isolated from blood plasma of patients with breast cancer or lung cancer. The cleavage of the purified factors with trypsin and purification of the active fragments were carried out by the following procedure:

le;2qTo prevent adsorption loss of the peptide during lyophilization, the SCM factor was digested with trypsin in the presence of HPLC eluants. Trypsin digestion was carried out in 0.1M Tris-HCl buffer, pH 8.3, at 37° C. for 24 hours using 10 percent by weight of trypsin. The digest was diluted fourfold with 0.1 volume percent aqueous trifluoroacetic acid, and was injected into an Applied Biosystems 130A microflow HPLC-separation system. The tryptic fragments were separated using an AQUAPORE™ RP-300 column (200 mm×2.1 mm). For the elution of the fragments, the mobile phase solvents were:

Phase A: 0.1 volume percent aqueous trifluoroacetic acid (TFA).

Phase B: 0.09 volume percent TFA in aqueous 70% acetonitrile.

The mobile phase flow rate was 50 µl per minute and the composition profile was 10 minutes of 96 volume percent Phase A, 4 volume percent Phase B, followed by a linear elution gradient comprising a 30 min linear increase in Phase B at a 3 volume percent per minute rate. The SCM-active tryptic peptide fragment eluted at 69.6 volume percent of Phase B and 30.4 volume percent of Phase A in a total volume of about 30 microliters.

le;2qThe tryptic peptide cleaved from the SCM factor purified from patients with lung cancer was tested for SCM activity and found to be fully active. By comparison with the sequences of the entire isolated SCM factors determined in Example 6, these tryptic peptides were found to represent amino acids 8–22 of the SCM factor molecule.

le;2qThe tryptic peptide obtained from SCM factor from plasma of patients with lung cancer, whose purification was described above, was fully active in the standard SCM test. Its activity was not limited to lymphocytes from patients with lung cancer, as it crossreacted fully when tested with lymphocytes from a patient with adenocarcinoma of the breast.

EXAMPLE 6

Amino Acid Sequences of Isolated SCM Factors le;2qThe amino acid sequences of isolated SCM factors, determined from purified preparations from blood plasmas of 12 different cancers, are presented in Table 1. The sequences were determined by an automated Edman degradation procedure, using the Applied Biosystems 477A protein sequencer coupled with an online 120A PTH-amino acid analyzer. Sequence-calling software was used to establish the amino acid residue at each cycle. The sequences of the SCM-factor peptides were obtained in repetitive analyses of two to three different preparations, isolated and purified to homogeneity, from pooled blood plasmas of about 5 to 50 different patients with a diagnosis of the same type of cancer. Amino acid residues designated in brackets below the primary, most significant residue detected at the particular degradation cycle represent secondary amino acid residues present in some of the degradation cycles in significant amounts. These secondary residues may indicate the presence of genetic polymorphisms of the SCM factors from individual blood donors contained in the sample pool that was used for sequencing; many, but not all, of the substitutions in these polymorphisms are conservative substitutions. In two cases, where a total of 35 amino acids were seen, the last six were weak. This indicates that two separate factors were present in the preparations, one of 29 amino acids, and a second of up to 35 amino acids. These two preparations were from donors with cancer of the prostate and seminoma of the testes. In some cases, no amino acid was seen in a particular cycle, designated by "X." These amino acids are most likely cysteine, and are otherwise referred to as cysteine (C). This is because of the 20 common amino acids, cysteine is the only one not detectable by the Edman degradation procedure. In the following tables, "Ca" indicates "cancer".

TABLE 1

AMINO ACID SEQUENCES OF PURIFIED ISOLATED SCM FACTORS

```
                           10              20              30
Ca-BREAST:    V I P P E V K F N K P F V F L M I D Q N T K T P L F M G K (SEQ ID NO: 12)
              (M)                                 (V)
```

TABLE 1-continued

AMINO ACID SEQUENCES OF PURIFIED ISOLATED SCM FACTORS

| | |
|---|---|
| Ca-LUNG: | M I P P E V K F N K P F V F L M I D Q N T K V P L F M G K (SEQ ID NO: 2)<br>(T) |
| Ca-COLON: | M I P P E V K F N K P F V F L M I D Q N T K V P L F M G K (SEQ ID NO: 2)<br>(D) |
| MELANOMA: | M I P P E V K F N K P F V F L M I D Q N T K X P X F M G X (SEQ ID NO: 9) |
| SCC-CERVIX: | M I P P E V K F N K P F V F L M I D Q N T K V P L F M G K (SEQ ID NO: 2)<br>(S) |
| Ca-OVARY: | M I P P E V K F N K P F V F L M I D Q N T K X X L F M G K (SEQ ID NO: 13)<br>(V) |
| Ca-UTERUS: | R I P P E V K F N K P F V F L M I D Q N T K R P L F M G K (SEQ ID NO: 14)<br>(S) |
| Ca-PANCREAS: | V I P P E V K F N K P F V F L M I D Q N T K X P L F M G K (SEQ ID NO: 10) |
| Ca-RENAL: | V I P P E V K F N X P F V F L M I D Q N T K V P L F M G K (SEQ ID NO: 11) |
| Ca-GASTRIC:<br>(SARCOMA) | R I P P E V K F N K P F V F L M I D Q N T K X P X F M G X (V V N X T E)<br>(S)     W (SEQ ID NOS: 15 & 16) |
| Ca-PROSTATE: | V I P P E V K F N K P F V F L M I E Q N T K S P L F M G K (V V N P T Q)<br>(S)     W (SEQ ID NOS: 17 & 18) |
| Ca-TESTIS:<br>(SEMINOMA) | S I P P E V K F N K P F V F L M I E Q N T K S P L F M G K V V N P T Q<br>(V) (SEQ ID NO: 19) |

EXAMPLE 7

SCM Activity of Synthetic SCM Factor

A synthetic SCM factor, representing the "consensus sequence" of M-I-P-P-E-V-K-F-N-K-P-F-V-F-L-L-I-D-Q-N-T-K-V-P-L-F-M-G-K (SEQ ID NO: 2), was synthesized using conventional solid-phase peptide synthesis techniques. Such techniques are described, for example, in M. Bodanszky, "Peptide Chemistry" (Springer-Verlag, Berlin, 1988), Ch. 10, "Solid Phase Peptide Synthesis."

The SCM activity of this synthetic SCM factor was tested by the standard SCM test. The synthetic SCM factor was fully active in the SCM test; this activity was specific for lymphocytes from cancer patients.

EXAMPLE 7

Fragments of Synthetic SCM Factor

Peptides representing distinct fragments of the synthetic SCM factor of Example 7 were synthesized by conventional solid-phase peptide synthesis techniques. These peptides were designated F1–F5 and have the following sequences:

F1: M-I-P-P-E-V-K-F-N-K-P-F-V-F-L-M-D-Q-N-T-K (SEQ ID NO: 4);

F2: F-N-K-P-F-V-F-L-M-I-D-Q-N-T-K-V-P-L-F-M-G-K (SEQ ID NO: 5);

F3: F-N-K-P-F-V-F-L-M-I-D-Q-N-T-K (SEQ ID NO: 6);

F4: F-L-M-I-D-Q-N-T-K (SEQ ID NO: 3); and

F5: M-I-P-P-E-V-K-F-N-K-P-F-V-F (SEQ ID NO: 7).

These fragments represented the following portions of the complete synthetic SCM molecule: F1, amino acids 1–22; F2, amino acids 8–29; F3, amino acids 8–22; F4, amino acids 14–22; and F5, amino acids 1–13.

Fragments F1, F2, F3, and F4 were all fully active in the SCM test, while fragment F5 was inactive. For fragments F1 through F4, the expected specificity of the SCM response was maintained, as these fragments gave no decrease in fluorescence polarization when used to challenge lymphocytes isolated from donors free of malignancy.

Of the peptides representing active fragments of the synthetic SCM molecule, the smallest is F4, residues 14–22. All of the other active peptides include this segment, while F5, which does not have this segment, is inactive. Accordingly, residues 14–22 can be considered to be the active site of the synthetic SCM-factor molecule. Significantly, this region of the peptide is virtually invariant in the isolated SCM factors, except for the extremely conservative substitution of glutamic acid (E) for aspartic acid (D) at position 18 in two of the factors.

EXAMPLE 9

Preparation of Antibodies to Synthetic SCM Factor

The synthetic SCM factor molecule was used to immunize experimental animals. Both pure synthetic SCM-factor molecules and SCM-factor molecules conjugated to the carrier keyhole limpet hemocyanin (KLH) via an added carboxy-terminal cysteine using N-succinimidyl bromoacetate as the cross-linking agent. These immunogens were used to immunize female New Zealand rabbits. Both immunogens were diluted for primary immunization to 1.0 mg/ml with sterile PBS, combined with an equal volume of Freund's complete adjuvant, and emulsified. For primary immunization, a total of 25 µg or 50 µg of either synthetic SCM factor or synthetic SCM factor conjugated with KLH (SCM-KLH) was injected into each rabbit; two rabbits were used for each dose range. The inoculate was administered at 0.2 ml into two legs intramuscularly and over a minimum of 12 dorsal sites subcutaneously at 0.2 ml per site. One month later, the first booster injection was administered. Synthetic SCM factor and SCM-KLH were each administered with an equal-volume mixture of Freund's complete and incomplete adjuvants and emulsified. The booster inoculates were injected via intramuscular and subcutaneous sites similar to those used for primary inoculations. Total doses of 25 μg or 50 μg of immunogen per rabbit were administered in the booster injections.

Blood samples taken 10 weeks after primary immunization yielded antisera containing higher amounts of immunoglobulins (IgG) from those animals injected with 50 μg of immunogen than from those animals injected with 25 μg of immunogen. Radial immunodiffusion tests, conducted as described in W. Becker, "Determination of Antisera Titres Using the Single Radial Immunodiffusion Method," *Immunochemistry* 6, 539 (1969), gave precipitation reactions against the unconjugated SCM factor and SCM factor conjugated to bovine serum albumin (BSA).

To separate the immunoglobulins containing the desired antibodies from the antisera, the immunoglobulins were first precipitated with an equal volume of saturated ammonium sulphate. The precipitates were then dissolved in 0.9% NaCl. To remove ammonium sulphate, the antibody-containing solutions were either dialyzed or ultrafiltered 10 times through an AMICON™ membrane filter with a 5000-dalton molecular weight cutoff. Antibodies were kept frozen at −40° C. until use.

EXAMPLE 10

ELISA Assay for SCM Factor

A double-antibody enzyme-linked competitive immunosorbent assay (ELISA) was developed for detection of SCM factor by the use of antibodies raised against SCM factor (Example 9). The ELISA assay is depicted schematically in FIG. 1. In the first step, SCM factor is attached to a solid phase such as plastic, typically by passive adsorption. In the second step, the sample to be assayed, along with a limited quantity of the anti-SCM antibody, is added. After a thorough washing, an excess of the labeled second antibody, goat anti-rabbit IgG labeled with the enzyme alkaline phosphatase, is then added in the third step. The substrate for alkaline phosphatase, p-nitrophenylphosphate, is then added, and the absorbance at 405 nm ($A_{405}$) is measured. In this assay, any free SCM factor added at the second step competes with the SCM factor adsorbed to the solid phase. Only the solid-phase SCM to which the first and second antibodies are bound yields color. Therefore, the higher is the concentration of SCM factor in the test sample, the lower is the measured $A_{405}$. This is typical of a competitive assay.

Variations on this procedure have been employed to detect SCM molecules in cancer cells, supernatants of growth culture media, blood plasma preparations from cancer patients, and purified extracts of SCM from various sources.

EXAMPLE 11

Activity of Anti-SCM Antibodies

Figure 2:
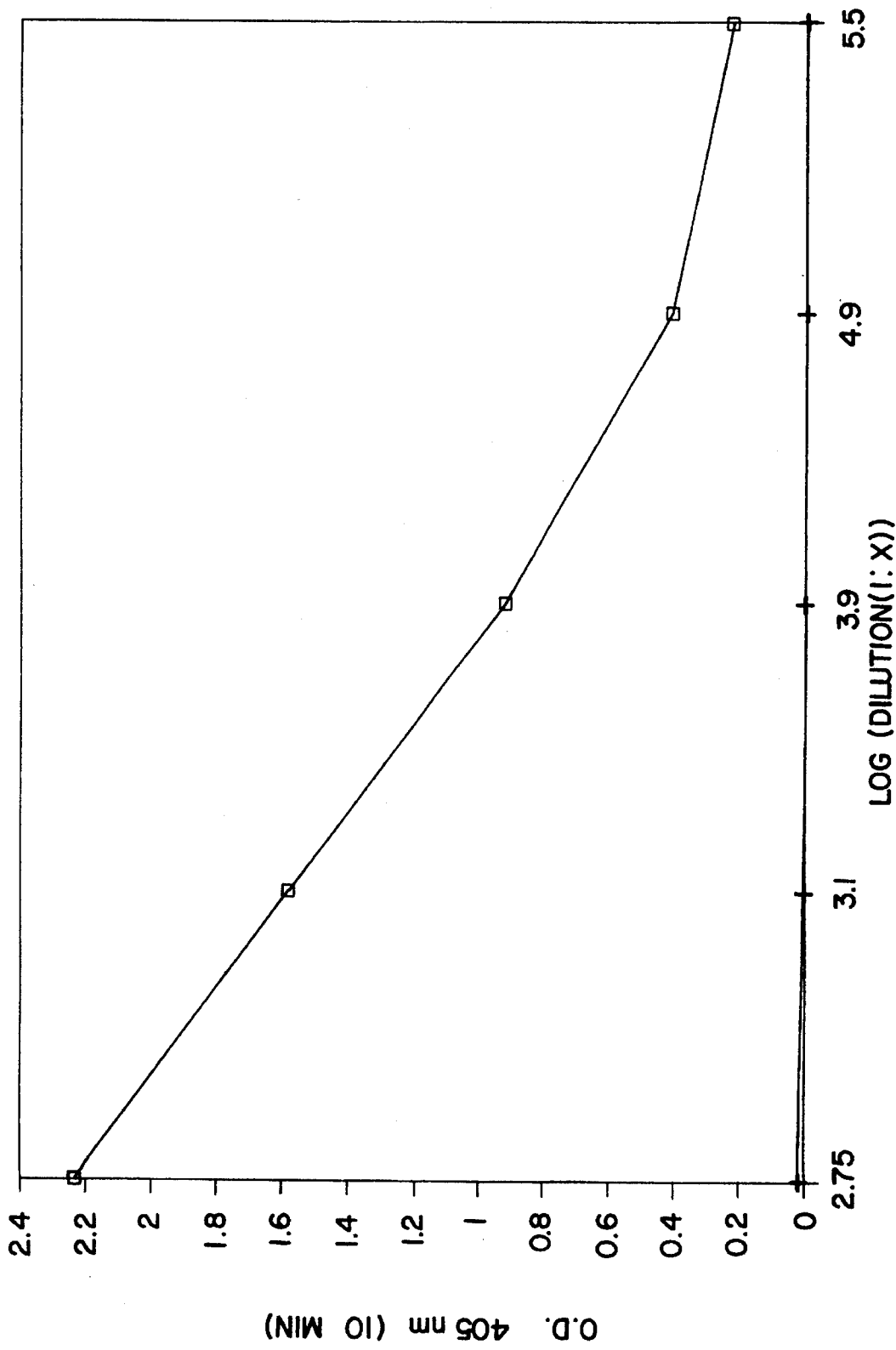
FIG. 2 shows the results obtained from an experiment in which the reactivity of antiserum raised against unconjugated SCM factor, as determined by absorbance at 405 nm in a version of the ELISA assay, was measured as a function of the dilution of the antiserum.

The activity of the antibodies of Example 9 raised against both unconjugated SCM factor and the KLH-SCM factor conjugate was determined by a variation of the ELISA assay of Example 10. Different dilutions of the antibodies were used, and no sample representing free SCM was added to the assay. The results are shown in FIG. 2 for the antiserum raised against unconjugated SCM factor, and in FIG. 3 for the KLH-SCM factor conjugate. As can be seen, both antibody preparations were active against purified SCM factor.

EXAMPLE 12

Determination of SCM-Factor Levels in Ultrafiltrates of Blood Plasmas by ELISA Assay The level of SCM factor was determined in a number of ultrafiltrates of blood plasmas from both healthy donors and cancer patients. Ultrafiltrates of blood plasmas from 12 cancer patients and 12 normal, healthy donors were prepared by filtration through an AMICON™ YM2 membrane filter with a 1000-dalton molecular weight cutoff. The level of SCM factor was assayed immunochemically by the ELISA assay of Example 10. The results are shown in Table 2. The levels of SCM factor detected by the ELISA assay were in the nanogram range per milliliter of ultrafiltrate. In the ultrafiltrates from donors with cancer, they were from 4.8 to 25.5 ng/ml. In normal, healthy donors, the levels of SCM factor were either below the minimum detectable level or up to a maximum of 1.85 ng/ml.

TABLE 2

LEVELS OF SCM FACTOR IN AMICON ® YM2
ULTRAFILTRATES OF BLOOD PLASMAS FROM
CANCER PATIENTS AND NORMAL, HEALTHY DONORS
AS DETECTED BY ANTI-SCM FACTOR
ANTIBODIES IN COMPETITIVE ELISA ASSAYS

| Diagnosis of Blood Donor | Donor's Sex and Age | | SCM Factor ng/ml |
|---|---|---|---|
| Ca-Breast | F | 39 | 12.0 |
| Ca-Breast | F | 50 | 10.1 |
| Ca-Breast | F | 49 | 7.0 |
| Ca-Lung | F | 76 | 13.4 |
| Ca-Lung | F | 67 | 8.7 |
| Ca-Lung | M | 47 | 5.5 |
| Ca-Pancreas | F | 50 | 8.5 |
| Ca-Colon | M | 42 | 4.8 |
| Ca-Colon | M | 44 | 14.0 |
| Ca-Colon | F | 60 | 10.5 |
| Malignant Melanoma | F | 38 | 15.7 |
| Malignant Melanoma | F | 50 | 25.5 |
| Normal Healthy | M | 31 | ND[a] |
| Normal Healthy | M | 49 | ND |
| Normal Healthy | M | 26 | 0.60 |
| Normal Healthy | M | 38 | 1.85 |
| Normal Healthy | M | 29 | 1.03 |
| Normal Healthy | M | 36 | 1.65 |
| Normal Healthy | F | 27 | 0.22 |
| Normal Healthy | F | 32 | 0.82 |
| Normal Healthy | M | 34 | ND |
| Normal Healthy | M | 46 | 0.22 |

[a]ND = none detected

EXAMPLE 13

Reactivity of SCM Factor Secreted from Human cancer Cells In Culture with Anti-SCM-factor Antibodies The SCM factors secreted from human cancer cells in culture also reacted with the anti-SCM antibody of Example 9. A noncompetitive variation of the ELISA assay of Example 10 was used. In this noncompetitive version of the ELISA assay, the assay was performed directly on the eluate from the RP-HPLC purification step that remained adsorbed to the Eppendorf collection tubes after loading of the bulk of the eluates onto the sequenator disk. No other SCM factor was added, and there was no additional sample added to the assay. This version of the SCM ELISA assay is noncompetitive; the larger is the quantity of SCM factor adsorbed to the Eppendorf tubes, the higher is the measured $A_{405}$. The results, shown in Table 3, clearly indicate the presence of material able to react with anti-SCM antibody in these fractions.

TABLE 3

ELISA ASSAYS ON SCM FACTOR IN RP-HPLC ELUATES PURIFIED FROM CULTURE MEDIA OF CANCER CELLS

| Origin of Eluate | Sample Number | ELISA $A_{405}$ Signal/Background Ratio[a] |
|---|---|---|
| MCF7 Breast Cancer Cells | 1 | 43 |
| MCF7 Breast Cancer Cells | 2 | 17 |
| MCF7 Breast Cancer Cells | 3 | 71 |
| HCT80 Colon Cancer Cells | 1 | 34 |
| HCT80 Colon Cancer Cells | 2 | 12 |

[a]Background is ELISA $A_{405}$ in tubes without adsorbed SCM factor.

fibrosarcoma cells. This data is presented in Table 5.

TABLE 4

SCM FACTOR IN HUMAN CANCER CELLS IN CULTURE AS DETECTED BY ELISA ASSAYS USING ANTI-SCM FACTOR ANTIBODY

| Human Cancer Cell Line ($4 \times 10^6$ cells) | ELISA $A_{405}$ Ratio[a] |
|---|---|
| MCF7 Breast Cancer Cells | 6.0 |
| MCF7 Breast Cancer Cells | 10.0 |
| MCF7 Breast Cancer Cells | 7.0 |
| T1080 Fibrosarcoma Cells | 6.5 |
| A2780 Ovary Cancer Cells | 4.6 |
| HCT80 Colon Cancer Cells | 3.0 |

[a]ELISA $A_{405}$ Ratio = $\dfrac{\text{ELISA } A_{405} \text{ (cells + antibody)}}{\text{ELISA } A_{405} \text{ (cells - antibody)}}$

TABLE 5

EFFECT OF CYCLOHEXIMIDE ON SCM FACTOR SYNTHESIS IN HUMAN CANCER CELLS IN CULTURE AS DETECTED BY ELISA ASSAYS USING ANTI-SCM FACTOR ANTIBODY

| Cancer Cells Line ($4 \times 10^6$ cells) | Cycloheximide ($\mu$g/$10^6$ cells) | Incubation (hrs) | Corrected $A_{405}$* | Corrected $A_{405}$ As % of Control |
|---|---|---|---|---|
| MCF7 Breast Cancer | 0 | 0 | 2.0716 | 100.0 |
| MCF7 Breast Cancer | 20 | 3 | 1.8893 | 91.2 |
| MCF7 Breast Cancer | 0 | 0 | 0.9654 | 100.0 |
| MCF7 Breast Cancer | 50 | 16 | 0.7217 | 74.7 |
| T1080 Fibrosarcoma | 0 | 0 | 1.5060 | 100.0 |
| T1080 Fibrosarcoma | 50 | 16 | 0.9940 | 66.0 |

[a]Corrected $A_{405}$ = (ELISA $A_{405}$ in presence of cells) - (ELISA $A_{405}$ in absence of cells)

EXAMPLE 14

Detection of SCM Factor in Human Cancer Cells In Culture by ELISA Assay

Human cancer cells in culture were directly shown to contain SCM-factor molecules by antibody reactivity. Washed cells from monolayered cultures of several human cancer cells: MCF7 breast cancer cells; T1080 fibrosarcoma cells; A2780 ovarian cancer cells; and HCT80 colon cancer cells, were assayed directly by the noncompetitive ELISA assay procedure of Example 13. The data is presented in Table 4. The calculated ELISA absorbance ratios (i.e., the absorbance in the presence of anti-SCM antibody divided by the absorbance in the absence of anti-SCM antibody, which are a relative measure of the amounts of SCM factor per $4 \times 10^6$ cells) showed that different cancer cell lines produced, under identical conditions, different amounts of SCM factor.

Treatment of cultured cancer cells with the protein synthesis inhibitor cycloheximide indicated that inhibition of protein synthesis decreased the concentration of SCM factor associated with the cultured cancer cells. The decrease was 25.3% for MCF7 breast cancer cells and 34% for T1080

EXAMPLE 15

Detection of SCM-Factor peptides in Cultured Cancer Cells in the Presence $\alpha_1$-PI Molecules by Two-Analyte Assay SCM factor peptides were detected in cultured cancer cells in the presence of $\alpha_1$-PI molecules by a two-analyte assay. Antibodies were raised against a synthetic peptide representing the amino-terminal 19 amino acids of human $\alpha_1$-PI conjugated to keyhole limpet hemocyanin. The amino acid sequence of this region of the $\alpha_1$-PI molecule lacks any substantial degree of homology with the amino acid sequence of either the naturally isolated or the synthetic SCM-factor peptides. The synthetic peptide was synthesized by standard solid-phase synthetic methods. For purification of the antibody to the amino-terminal region of $\alpha_1$-PI, the peptide was coupled to biotin-LC (Pierce Chemical Company, Rockford, Ill.), at the amino-terminal end. The peptide was bound to an avidin-agarose gel (Pierce) and used for affinity purification of the antibody.

For the assay, duplicate cell aliquots (supernatants from 1-ml aliquots containing $5 \times 10^6$ cells/ml) were dried in Eppendorf tubes so that the remaining protein was absorbed to the plastic tubes. Duplicate cell aliquots were incubated with either rabbit IgG anti-SCM (Example 9) or anti-α₁-PI antibodies as described above (0.6 ml of antibody solution at a 1:1000 dilution for each antibody) for 3 hours at room temperature, with shaking, in an incubation buffer containing phosphate buffered saline (PBS) without calcium or magnesium, with 3% bovine serum albumin and 0.5% Tween 20, pH 7.2 (IB). The tubes were washed once with IB and twice with 0.9% NaCl phosphate buffered saline containing 0.5% Tween 20. The tubes were then incubated with 0.6 ml of a 1:1000 dilution in IB of goat anti-rabbit IgG-alkaline phosphatase conjugate (Sigma) for 1 hour at room temperature with shaking. The alkaline phosphatase substrate p-nitrophenyl phosphate (Sigma 104™, Sigma) was added (1 ml per assay) and absorbance at 405 nm was measured after an incubation of 30 minutes to 1 hour.

The results were expressed as a ratio of net absorbances. The ratio was calculated by first subtracting the $A_{405}$ values of controls (cells without the first antibody) from the $A_{405}$ values obtained from the incubations with both antibodies to obtain net absorbances for the anti-$\alpha_1$-PI and anti-SCM factor aliquots. Then, the net absorbance for the anti-$\alpha_1$-PI aliquot is divided by the net absorbance for the anti-SCM factor aliquot. A ratio of less than about 1 indicates the presence of SCM factor peptides.

The results are shown in Table 6. These results show that SCM factor peptides were detected only in the malignant and transformed cells, and not in the normal fibroblast cell strains.

TABLE 6

TWO-ANALYTE TEST FOR THE DETECTION OF SCM FACTOR PEPTIDES IN THE PRESENCE OF $\alpha_1$-PI IN CANCER AND NORMAL HUMAN CELLS

| Cell Line | EIA $A_{405}$ Ratio: Anti-$\alpha_1$-PI(1-19)/Anti-SCM |
|---|---|
| Malme-3 Normal Skin Fibroblasts | 2.60 |
| Malme-3M Malignant Melanoma | 0.78 |
| Normal Lung WI-38 Fibroblasts | 1.60 |
| SV-40 Transformed Lung WI-38 Fibroblasts | 0.43 |

TABLE 6-continued

TWO-ANALYTE TEST FOR THE DETECTION OF SCM FACTOR PEPTIDES IN THE PRESENCE OF $\alpha_1$-PI IN CANCER AND NORMAL HUMAN CELLS

| Cell Line | EIA $A_{405}$ Ratio: Anti-$\alpha_1$-PI(1-19)/Anti-SCM |
|---|---|
| HCT80₅ Colon Cancer Cells | 0.71 |

ADVANTAGES OF THE PRESENT INVENTION

The availability of antibodies specific for the SCM factor or portions thereof provides a convenient, specific, and rapid way of detecting the SCM factor in a wide variety of cells and biological fluids. Because the presence of SCM factors in cells is closely correlated with their malignant state, the use of immunoassays that can detect these factors provides an improved test for cancer. The immunoassay can be used to detect specific SCM factors or can detect the invariant portion of the SCM factor that is virtually identical in SCM factors isolated from all cancer-affected tissues.

Monoclonal antibodies can be prepared using antibody-producing cells immunized in accordance with the present invention. These monoclonal antibodies are especially useful in the detection of SCM factors in vivo.

Additionally, the two-analyte immunoassay provides a sensitive and specific test for the detection of SCM-active cancer recognition peptides even in a background in which the serine protease inhibitor $\alpha_1$-PI is present. This protein contains, at its carboxy-terminal portion, a sequence partially homologous with the sequence of SCM-factor peptides, and therefore, would crossreact with antibodies raised against the SCM-factor peptides, thus making it difficult to detect and/or quantitate the amount of the antibody bound to the SCM-factor peptides produced by cancer cells.

Although the present invention has been described in considerable detail with regard to certain preferred versions thereof, other versions are possible. Therefore, the spirit and scope of the appended claims should not be limited to the descriptions of the preferred versions contained herein.

We claim:

1. A method for detecting a selected peptide factor active in the structuredness of the cytoplasmic matrix (SCM) test in a sample that may also contain a second peptide sequence that is partially homologous to the selected peptide factor, comprising the steps of:

(a) incubating a first aliquot of the sample with a first antibody capable of forming an antigen-antibody complex with a peptide factor active in the SCM test, the factor being a peptide of nine amino acid residues to 35 amino acid residues including a core sequence of nine amino acid residues having an amphipathicity profile substantially equivalent to that of the sequence F-L-M-I-D-Q-N-T-K, wherein the sixth amino acid of the core sequence is selected from the group consisting of Q and N, the seventh amino acid of the core sequence is selected from the group consisting of N and Q, and the ninth amino acid of the core sequence is selected from the group consisting of Q and R, the factor producing at least a 10% decrease in the intracellular fluorescence polarization value of lymphocytes capable of responding in the SCM test as isolated from donors afflicted with cancer to bind the first antibody to the peptide factor and to the partially homologous peptide sequence in the first aliquot;

(b) incubating a second aliquot of the sample with a second antibody specific for a portion of the partially homologous sequence lacking any substantial homology with any portion of the peptide factor active in the SCM test to bind the second antibody only to the partially homologous peptide sequence in the second aliquot; and (c) detecting a peptide factor active in the SCM test by an immunochemical reaction by comparing the quantity of the first antibody bound to the first aliquot with the quantity of the second antibody bound to the second aliquot.

2. The method of claim 1 where the first antibody is an antibody that specifically binds a peptide selected from the group consisting of M-I-P-P-E-V-K-F-N-K-P-F-V-F-L-M-I-D-Q-N-T-K-V-P-L-F-M-G-K (SEQ ID NO: 2) and a peptide related thereto by one or more conservative amino acid substitutions.

3. The method of claim 2 where the first antibody specifically binds the peptide M-I-P-P-E-V-K-F-N-K-P-F-V-F-L-M-I-D-Q-N-T-K-V-P-L-F-M-G-K (SEQ ID NO: 2).

4. The method of claim 1 where the first antibody specifically binds the peptide F-L-M-I-D-Q-N-T-K (SEQ ID NO: 3).

5. The method of claim 1 where the first antibody is selected from the group consisting of:

(i) an antibody produced by immunization of an antibody-producing animal with the peptide M-I-P-P-E-V-K-F-N-K-P-F-V-F-L-M-I-D-Q-N-T-K-V-P-L-F-M-G-K-C (SEQ ID NO: 1) conjugated at its carboxy-terminal cysteine residue to a carrier protein; and (ii) an antibody produced by immunization of an antibody producing animal with the peptide M-I-P-P-E-V-K-F-N-K-P-F-V-F-L-M-I-D-Q-N-T-K-V-P-L-F-M-G-K (SEQ ID NO: 2).

6. The method of claim 1 where the antibody specific for the cancer-recognition factor is a monoclonal antibody.

7. The method of claim 1 wherein the sample is a cellular sample.

8. The method of claim 1 wherein the region of the partially homologous peptide that lacks any substantial homology with any portion of the sequence of the peptide factor active in the SCM test is the amino-terminal portion of $\alpha_1$-antitrypsin, and wherein the second antibody specifically binds the amino-terminal portion of $\alpha_1$-antitrypsin.

9. The method of claim 8 wherein the amino-terminal portion of the $\alpha$-antitrypsin is the amino-terminal 19 amino acids.

10. The method of claim 2 where the step of comparing the quantity of the first antibody specific for the cancer-recognition factor and bound to: (i) the cancer-recognition factor and (ii) the partially homologous peptide sequence in the first aliquot to the quantity of the second antibody specific for the amino-terminal portion of the partially homologous peptide sequence and bound only to the partially homologous peptide sequence in the second aliquot comprises:

(i) reacting the incubated aliquots of steps (a) and (b) separately with a detection antibody that is specific for both the first and second antibodies, the detection antibody being coupled to a detectable label; and (ii) detecting the label.

11. The method of claim 10 wherein the first and second antibodies are both rabbit IgG antibodies and the detection antibody is an antibody specific for rabbit IgG.

12. The method of claim 10 wherein the label is selected from the group consisting of an enzyme label, a fluorescent label, a radioactive label, a colorimetric label, a metal sol label and a chemiluminescent label.

13. The method of claim 12 wherein the label is an enzyme label.

14. The method of claim 13 wherein the enzyme is alkaline phosphatase.

15. The method of claim 1 wherein the first and second antibodies are each coupled to a member of the avidin-biotin specific binding pair, the first and second antibodies being coupled to the same binding pair member, and wherein the step of comparing the quantity of the first antibody bound to the first aliquot with the quantity of the second antibody bound to the second aliquot comprises:

(i) reacting the incubated first and second aliquot separately with a detectable label, the detectable label being coupled to the specific binding pair member complementary to the specific binding pair member that is coupled to the first and second antibody; and (ii) separately detecting the label bound to the first and second aliquots in order to determine the presence of the cancer-recognition factor.

16. The method of claim 1 wherein the partially homologous peptide sequence comprises at least a portion of the sequence of $\alpha_1$-antitrypsin smaller than the intact $\alpha_1$-antitrypsin molecule.

17. A method for detecting a peptide factor active in the structuredness of the cytoplasmic matrix (SCM) test in the presence of $\alpha_1$-antitrypsin, comprising the steps of:

(a) incubating a first aliquot of cells with a first rabbit IgG antibody capable of forming an antigen-antibody complex with the peptide factor active in the SCM test to bind the first antibody to the cells of the first aliquot, the first antibody being selected from the group consisting of: (i) an antibody produced by immunization with a peptide of the sequence M-I-P-P-E-V-K-F-N-K-P-F-V-F-L-M-I-D-Q-N-T-K-V-P-L-M-G-K-C (SEQ ID NO: 1) conjugated at its carboxy-terminal cysteine residue to a carrier protein; and (ii) an antibody produced by immunization with a peptide of the sequence M-I-P-P-E-V-K-F-N-K-P-F-V-F-L-M-I-D-Q-N-T-K-V-P-L-F-M-G-K (SEQ ID NO: 2), the first antibody binding both to the peptide factor active in the SCM test and the $\alpha_1$-antitrypsin in the first aliquot;

(b) incubating a second aliquot of the cells with a second rabbit IgG antibody specific for the amino-terminal 19-amino acid sequence of $\alpha_1$-antitrypsin, the amino-terminal 19-amino acid sequence of $\alpha_1$-antitrypsin lacking any substantial homology with any portion of the sequence of the peptide factor active in the SCM test, the second antibody binding only to the $\alpha_1$-antitrypsin in the second aliquot;

(c) reacting the incubated aliquots of steps (a) and (b) separately, each incubated aliquot being reacted with an antibody specific for rabbit IgG antibody coupled to an enzyme label to label the first antibody bound to the first aliquot and the second antibody bound to the second aliquot;

(d) incubating the bound enzyme-labeled antibodies of the first and second aliquots separately, each with an indicator that yields a detectable product in response to enzymatic activity of the enzyme; and (e) detecting the peptide factor by an immunochemical reaction by comparing the quantity of detectable product produced by the first and second aliquot.

18. The method of claim 17 wherein the enzyme label is alkaline phosphatase and the substrate necessary to yield a detectable label is p-nitrophenyl phosphate.

19. An antibody specifically binding a peptide factor active in the structuredness of the cytoplasmic matrix (SCM) test, the factor being a peptide of at least 9 amino acid residues, including a core sequence of 9 amino acid residues, the core sequence being F-$X_{15}$-M-$X_{17}$-$X_{18}$-$X_{19}$-$X_{20}$-$X_{21}$-K, wherein $X_{15}$ and $X_{17}$ are each independently selected from the group consisting of I, L, and V; $X_{18}$ is selected from the group consisting of D and E; $X_{19}$ and $X_{20}$ are each independently selected from the group consisting of Q and N; and $X_{21}$ is selected from the group consisting of S and T, the factor capable of producing at least a 10% decrease of the intracellular florescence polarization value of lymphocytes capable of responding in the SCM test isolated from donors afflicted with cancer.

20. The antibody of claim 19 that is a monoclonal antibody.

21. The antibody of claim 19 wherein the core sequence is F-L-M-I-D-Q-N-T-K (SEQ ID NO: 3).

22. The antibody of claim 19 wherein the peptide factor active in the SCM test comprises 9 amino acid residues and comprises the sequence F-$X_{15}$-M-$X_{15}$-M-$X_{17}$-$X_{18}$-$X_{19}$-$X_{20}$-$X_{21}$-K.

23. The antibody of claim 22 wherein the peptide factor active in the SCM test has the sequence F-L-M-I-D-Q-M-T-K (SEQ ID NO: 3).

24. The antibody of claim 19 wherein the peptide factor active in the SCM test comprises 15 amino acid residues and comprises the sequence F-$X_9$-K-P-F-$X_{13}$-F-$X_{15}$-M-$X_{17}$-$X_{18}$-$X_{19}$-$X_{20}$-$X_{21}$-K, wherein $X_9$ is independently selected from the group consisting of Q and N, and $X_{13}$ is independently selected from the group consisting of I, L and V.

25. The antibody of claim 24 wherein the peptide factor active in the SCM test comprises the sequence F-N-K-P-F-V-F-L-M-I-D-Q-N-T-K (SEQ ID NO: 6).

26. The antibody of claim 19 wherein the peptide factor active in the SCM test comprises 22 amino acid residues and comprises the sequence F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-K, wherein $X_9$ is independently selected from the group consisting of Q and N; and $X_{23}$ and $X_{25}$ are each independently selected from the group consisting of I, L, and V.

27. The antibody of claim 26 wherein the peptide factor active in the SCM test comprises the sequence F-N-K-P-F-V-F-L-M-I-D-Q-N-T-K-V-P-L-F-M-G-K (SEQ ID NO: 5).

28. The antibody of claim 19 wherein the peptide factor active in the SCM test comprises 22 amino acid residues and has the sequence M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-$X_{21}$-K, wherein $X_2$ and $X_6$ are each independently selected from the group consisting of I, L, and V; $X_5$ is independently selected from the group consisting of D and E; and $X_9$ is independently selected from the group consisting of Q and N.

29. The antibody of claim 28 wherein the peptide factor active in the SCM test comprises the sequence M-I-P-P-E-V-K-F-N-K-P-F-V-F-L-M-I-D-Q-N-T-K (SEQ ID NO: 4).

30. An antibody specifically binding a peptide selected from the group consisting of a peptide of the sequence M-I-P-P-E-V-K-F-N-K-P-F-V-F-L-M-I-D-Q-N-T-K-V-P-L-F-M-G-K (SEQ ID NO: 2) and a peptide related thereto by one or more conservative amino acid substitutions.

31. An antibody specifically binding a peptide factor active in the structuredness of the cytoplasmic matrix (SCM) test, the factor comprising a peptide of 29 amino acid residues and comprising an amino acid sequence of M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-K, wherein $X_2$, $X_6$, $X_{13}$, $X_{15}$, $X_{17}$, $X_{23}$, and $X_{25}$ are each independently selected from the group consisting of I, L, and V; $X_5$ and $X_{18}$ are each independently selected from the group consisting of D and E; $X_9$, $X_{19}$, and $X_{20}$ are each independently selected from the group consisting of Q and N; and $X_{21}$ is selected from the group consisting of S and T, the factor capable of producing at least a 10% decrease in the intracellular fluorescence polarization of lymphocytes capable of responding in the SCM test.

32. The antibody of claim 31 that is a monoclonal antibody.

33. The antibody of claim 31 wherein the peptide factor active in the SCM test has the sequence M-I-P-P-E-V-K-F-N-K-P-F-V-F-L-M-I-D-Q-N-T-K-V-P-L-F-M-G-K (SEQ ID NO: 2).

34. An antibody specifically binding a peptide factor active in the structuredness of the cytoplasmic matrix (SCM) test, the factor being from 29 to 35 amino acid residues in length, including a core sequence at amino acids 14–22 of F-L-M-I-$X_{18}$-Q-N-T-K, wherein $X_{18}$ is selected from the group consisting of D and E, the factor capable of producing at least a 10% decrease in the intracellular florescence polarization value of lymphocytes capable of responding in the SCM test.

35. The antibody of claim 34 wherein the peptide factor active in the SCM test comprises the sequence V-I-P-P-E-V-K-F-N-K-P-F-V-F-L-M-I-D-Q-N-T-K-V-P-L-F-M-G-K (SEQ ID NO: 8).

36. The antibody of claim 34 wherein the peptide factor active in the SCM test comprises the sequence M-I-P-P-E-V-K-F-N-K-P-F-V-F-L-M-I-D-Q-N-T-K-C-P-C-F-M-G-C (SEQ ID NO: 9).

37. The antibody of claim 34 wherein the peptide factor active in the SCM test comprises the sequence $X_1$-I-P-P-E-V-K-F-N-K-P-F-V-F-L-M-I-D-Q-N-P-K-C-C-L-F-M-G-K, wherein $X_1$ is selected from the group consisting of M and V.

38. The antibody of claim 34 wherein the peptide factor active in the SCM test comprises the sequence $X_1$-I-P-P-E-V-K-F-N-K-P-F-V-F-L-M-I-D-Q-N-T-K-R-P-F-M-G-K, wherein $X_1$ is selected from the group consisting of R and S.

39. The antibody of claim 34 wherein the peptide factor active in the SCM test comprises the sequence V-I-P-P-E-V-K-F-N-K-P-F-V-F-L-M-I-D-Q-N-T-K-C-P-L-F-M-G-K (SEQ ID NO: 10)

40. The antibody of claim 34 wherein the peptide factor active in the SCM test comprises the sequence V-I-P-P-E-V-K-F-N-C-P-F-V-F-L-M-I-D-Q-N-T-K-V-P-L-F-M-G-K (SEQ ID NO: 11).

41. The antibody of claim 34 wherein the peptide factor active in the SCM test is selected from the group consisting of peptides having amino acid sequences $X_1$-I-P-P-E-V-K-F-N-K-P-F-V-F-L-M-I-D-Q-N-T-K-C-P-C-F-M-G-C and $X_1$-I-P-P-E-V-K-F-N-K-P-F-V-F-L-M-I-D-Q-N-T-K-C-P-C-F-M-G-C-V-V-N-C-T-E, wherein $X_1$ is selected from the group consisting of R and S.

42. The antibody of claim 34 wherein the peptide factor active in the SCM test is selected from the group consisting of peptides having amino acid sequences $X_1$-I-P-P-E-V-K-F-N-K-P-F-V-F-L-M-I-E-Q-N-T-K-S-P-L-F-L-G-K and $X_1$-I-P-P-E-V-K-F-N-K-P-F-V-F-L-M-I-E-Q-N-T-K-S-P-L-F-M-G-K-V-V-N-P-T-Q, wherein $X_1$ is selected from the group consisting of V and S.

43. The antibody of claim 34 wherein the peptide factor active in the SCM test has the sequence $X_1$-I-P-P-E-V-K-F-N-K-P-F-V-F-L-M-I-E-Q-N-T-K-S-P-L-F-M-G-K-V-V-N-P-T-Q, wherein $X_1$ is selected from the group consisting of S and V.

44. The antibody of claim 34 that is a monoclonal antibody.

45. An antibody specific for a peptide factor active in the structuredness of the cytoplasmic matrix (SCM) test prepared by immunization of an antibody-producing animal with a peptide of the sequence M-I-P-P-E-V-K-F-N-K-P-F-V-F-L-M-I-D-Q-N-T-K-V-P-L-F-M-G-K-C (SEQ ID NO: 1) conjugated at its carboxy-terminal cysteine residue to a carrier protein.

46. The antibody of claim 45 that is a monoclonal antibody.

47. An antibody specific for a peptide factor active in the structuredness of the cytoplasmic matrix (SCM) test prepared by immunizing an antibody producing animal with a peptide of the sequence M-I-P-P-E-V-K-F-N-K-P-F-V-F-L-M-I-D-Q-N-T-K-V-P-L-F-M-G-K (SEQ ID NO: 3).

48. The antibody of claim 47 that is a monoclonal antibody.

49. A method for determining the concentration of a peptide factor active in the structuredness of the cytoplasmic matrix (SCM) test comprising the steps of:

(a) mixing the body fluid and the antibody of claim 19;

(b) performing an immunoassay to determine the extent of reaction between the peptide factor in the body fluid and the antibody; and (c) detecting the reaction between the antibody and the peptide factor in the body fluid to determine the concentration of the peptide factor active in the SCM test in the body fluid without detecting intact $\alpha_1$-antitrypsin.

50. The method of claim 49 wherein the immunoassay is selected from the group consisting of radioimmunoassays, fluorescence immunoassays, chemiluminescence immunoassays, and enzyme-linked immunoassays.

51. The method of claim 50 that is an enzyme-linked immunoassay comprising:

(a) attaching the peptide factor or an immunologically equivalent analog thereof to a solid phase capable of binding protein;

(b) adding a body fluid to the solid phase;

(c) incubating the solid phase with a first antibody specific for the peptide factor;

(d) separating unbound body fluid components and first antibody from the solid phase;

(e) incubating the solid phase with a second antibody that is specific for the first antibody, the second antibody being labeled with an enzyme producing a colorimetrically detectable product when the enzyme is incubated with a substrate;

(f) adding the substrate for the enzyme; and (g) measuring the absorbance of the colorimetrically detectable product.

52. The method of claim 49 further comprising the step of removing $\alpha_1$-antitrypsin molecules from the body fluid before the mixing of the body fluid and the antibody.

53. A method for determining the concentration of a peptide factor active in the structuredness of the cytoplasmic matrix (SCM) test comprising the steps of:

(a) mixing the body fluid and the antibody of claim 30;

(b) performing an immunoassay to determine the extent of reaction between the peptide factor in the body fluid and the antibody; and (c) detecting the reaction between the antibody and the peptide factor in, the body fluid to determine the concentration of the peptide factor active in the SCM test in the body fluid without detecting intact $\alpha_1$-antitrypsin.

54. The method of claim 53 wherein the immunoassay is selected from the group consisting of radioimmunoassays, fluorescence immunoassays, chemiluminescence immunoassays, and enzyme-linked immunoassays.

55. The method of claim 54 that is an enzyme-linked immunoassay comprising:

(a) attaching the peptide factor or an immunologically equivalent analog thereof to a solid phase capable of binding protein;

(b) adding the body fluid to the solid phase;

(c) incubating the solid phase with a first antibody specific for the peptide factor;

(d) separating unbound body fluid components and first antibody from the solid phase;

(e) incubating the solid phase with a second antibody that is specific for the first antibody, the second antibody being labeled with an enzyme producing a colorimetrically detectable product when the enzyme is incubated with a substrate;

(f) adding the substrate for the enzyme; and (g) measuring the absorbance of the colorimetrically detectable product.

56. A method for determining the concentration of a peptide factor active in the structuredness of the cytoplasmic matrix (SCM) test comprising the steps of:

(a) mixing the body fluid and the antibody of claim 34;

(b) performing an immunoassay to determine the extent of reaction between the peptide factor in the body fluid and the antibody; and (c) detecting the reaction between the antibody and the peptide factor in the body fluid to determine the concentration of the peptide factor active in the SCM test in the body fluid without detecting intact $\alpha_1$-antitrypsin.

57. The method of claim 56 wherein the immunoassay is selected from the group consisting of radioimmunoassays, fluorescence immunoassays, chemiluminescence immunoassays, and enzyme-linked immunoassays.

58. The method of claim 57 that is an enzyme-linked immunoassay comprising:

(a) attaching the peptide factor or an immunologically equivalent analog thereof to a solid phase capable of binding protein;

(b) adding the body fluid to the solid phase;

(c) incubating the solid phase with a first antibody specific for the peptide factor;

(d) separating unbound body fluid components and first antibody from the solid phase;

(e) incubating the solid phase with a second antibody that is specific to the first antibody specific for the peptide factor, the second antibody being labeled with an enzyme producing a colorimetrically detectable product when the enzyme is incubated with a substrate;

(f) adding the substrate for the enzyme; and (g) measuring the absorbance of the colorimetrically detectable product.

59. A method for determining the concentration of a peptide factor active in the structuredness of the cytoplasmic matrix (SCM) test comprising the steps of:

(a) mixing the body fluid and the antibody of claim 35;

(b) performing an immunoassay to determine the extent of reaction between the peptide factor in the body fluid and the antibody; and (c) detecting the reaction between the antibody and the peptide factor in the body fluid to determine the concentration of the peptide factor active in the SCM test in the body fluid without detecting intact $\alpha_1$-antitrypsin.

60. The method of claim 59 wherein the immunoassay is selected from the group consisting of radioimmunoassays, fluorescence immunoassays, chemiluminescence immunoassays, and enzyme-linked immunoassays.

61. The method of claim 60 that is an enzyme-linked immunoassay comprising:

(a) attaching the peptide factor or an immunologically equivalent analog thereof to a solid phase capable of binding protein;

(b) adding the body fluid to the solid phase;

(c) incubating the solid phase with a first antibody specific with cancer-recognition factor;

(d) separating unbound body fluid components and first antibody from the solid phase;

(e) incubating the solid phase with a second antibody that is specific to the first antibody, the second antibody being labeled with an enzyme producing a colorimetrically detectable product when the enzyme is incubated with a substrate;

(f) adding the substrate for the enzyme; and (g) measuring the absorbance of the colorimetrically detectable product.

62. A method for determining the concentration of a peptide factor active in the structuredness of the cytoplasmic matrix (SCM) test comprising the steps of:

(a) mixing the body fluid and the antibody of claim 45;

(b) performing an immunoassay to determine the extent of reaction between the peptide factor in the body fluid and the antibody; and (c) detecting the reaction between the antibody and the peptide factor in the body fluid to determine the concentration of the peptide factor active in the SCM test in the body fluid without detecting intact $\alpha_1$-antitrypsin,

63. The method of claim 62 wherein the immunoassay is selected from the group consisting of radioimmunoassays, fluorescence immunoassays, chemiluminescence immunoassays, and enzyme-linked immunoassays.

64. The method of claim 63 that is an enzyme-linked immunoassay comprising:

(a) attaching the peptide factor or an immunologically equivalent analog thereof to a solid phase capable of binding protein;

(b) adding the body fluid to the solid phase;

(c) incubating the solid phase with a first antibody specific for the peptide factor;

(d) separating unbound body fluid components and first antibody from the solid phase;

(e) incubating the solid phase with a second antibody that is specific to the first antibody, the second antibody being labeled with an enzyme producing a colorimetrically detectable product when the enzyme is incubated with a substrate;

(f) adding the substrate for the enzyme; and (g) measuring the absorbance of the colorimetrically detectable product.

65. A method for determining the concentration of a peptide factor active in the structuredness of the cytoplasmic matrix (SCM) test comprising the steps of:

(a) mixing the body fluid and the antibody of claim 47;

(b) performing an immunoassay to determine the extent of reaction between the peptide factor in the body fluid and the antibody; and (c) detecting the reaction between the antibody and the peptide factor in the body fluid to determine the concentration of the peptide factor active in the SCM test in the body fluid without detecting intact $\alpha_1$-antitrypsin, 66. The method of claim 65 wherein the immunoassay is selected from the group consisting of radioimmunoassays, fluorescence immunoassays, chemiluminescence immunoassays, and enzyme-linked immunoassays.

67. The method of claim 66 that is an enzyme-linked immunoassay comprising:

(a) attaching the peptide factor or an immunologically equivalent analog thereof to a solid phase capable of binding protein;

(b) adding the body fluid to the solid phase;

(c) incubating the solid phase with a first antibody specific for the peptide factor;

(d) separating unbound body fluid components and first antibody from the solid phase;

(e) incubating the solid phase with a second antibody that is specific to the first antibody, the second antibody being labeled with an enzyme producing a colorimetrically detectable product when the enzyme is incubated with a substrate;

(f) adding the substrate for the enzyme; and (g) measuring the absorbance of the colorimetrically detectable product.

* * * * *

UNITED STATES PATENT AND TRADEMARK OFFICE
CERTIFICATE OF CORRECTION

PATENT NO. : 5,516,643

DATED : May 14, 1996

INVENTOR(S) : Cercek et al.

It is certified that error appears in the above-indentified patent and that said Letters Patent is hereby corrected as shown below:

Column 14, line 60, delete "x18" and insert --$X_{18}$--.

Column 19, line 57, delete "$X_{15}$" and insert --$X_{15}$--.

Column 23, line 67, delete "$a^1$-PI" and insert --$a_1$-PI--.

Column 28, line 5, delete "1e;2q" before the word "The".

Column 28, line 11, delete "1e;2q" before the word "The".

Column 28, line 25, delete "1e;2q" before the word "The".

Column 32, line 58, delete "cancer" and insert --Cancer--".

Column 34, Table 5, line 5, delete "Cells" and insert --Cell--.

Column 34, line 6, delete "$A_{405}$" and insert --$A_{405}^a$--.

Column 34, exhibit 15, line 46, delete "peptides" and insert --Peptides--.

UNITED STATES PATENT AND TRADEMARK OFFICE
CERTIFICATE OF CORRECTION

PATENT NO. : 5,516,643

DATED : May 14, 1996

INVENTOR(S) : Cercek et al

It is certified that error appears in the above-identified patent and that said Letters Patent is hereby corrected as shown below:

Column 34, line 47, insert --of-- after the word "Presence".

Column 50, claim 22, line 28, delete "$X_{15}$" and insert --$X_{15}$--.

Column 50, claim 24, line 35 delete "$X_{13}$" and insert --$X_{13}$--.

Column 50, claim 26, line 44 delete "$X_{13}$" and insert --$X_{13}$--.

Column 50, claim 28, line 54, delete "$X_9$" and insert --$X_9$--.

Column 51, claim 31, line 5, delete "$X_{17}$" and insert --$X_{17}$--.

Column 51, claim 31, line 6, delete "$X_{23}$" and insert --$X_{23}$--.

Signed and Sealed this

Fourth Day of March, 1997

Attest:

*Attesting Officer*

BRUCE LEHMAN

*Commissioner of Patents and Trademarks*